United States Patent [19]
Kovacevic et al.

[11] Patent Number: 5,814,503
[45] Date of Patent: Sep. 29, 1998

[54] FUSION PROTEINS COMPRISING CELL CYCLE REGULATORY PROTEINS

[75] Inventors: Steven Kovacevic, Indianapolis; Keith A. Otto, Greenwood; Ramachandra N. Rao, Indianapolis, all of Ind.

[73] Assignee: Eli Lilly and Company, Indianapolis, Ind.

[21] Appl. No.: 770,761

[22] Filed: Dec. 19, 1996

Related U.S. Application Data

[60] Provisional application No. 60/009,629 Jan. 5, 1996.
[51] Int. Cl.[6] ............................... C12N 9/12; C12N 15/52
[52] U.S. Cl. .................... 435/188; 435/69.7; 435/194; 530/350; 530/358; 536/23.4
[58] Field of Search .................................. 530/350, 358; 536/23.4; 435/69.7, 194, 188

[56] References Cited

PUBLICATIONS

Gadbois et al. 1995 Exp. Cell Research 220: 220–225.

*Primary Examiner*—Thomas M. Cunningham
*Assistant Examiner*—Martha Lubet
*Attorney, Agent, or Firm*—Paul J. Gaylo; David E. Boone

[57] ABSTRACT

The present invention provides novel fusion proteins comprising cyclins and CDKs. A preferred embodiment of the invention provides fusion proteins comprising human cyclin D1 and human CDK4. The fusion proteins of the invention optionally contain modifications, which facilitate their purification. Addition of histidine residues to selected constructs allows purification via immobilized metal affinity chromatography. Antigenic determinants allowing monoclonal antibody-based affinity chromatography purification are provided in selected embodiments of the invention. Protease cleavage sites are incorporated in selected constructs to allow cleavage of the regions incorporated in the cyclin-CDK fusion proteins for purification. Additional modifications which facilitate purification include strepavadin binding domains and antigenic determinants for antibody affinity chromatography.

5 Claims, 3 Drawing Sheets

FUSION PROTEINS COMPRISING CELL CYCLE REGULATORY PROTEINS

This application claims the benefit of U.S. Provisional Application Ser. No. 60/009,626; filed Jan. 5, 1996.

BACKGROUND OF THE INVENTION

The pivotal roles which cyclins and cyclin dependent kinases play in cell cycle regulation is well established. The initial interest in cyclins resulted from observations that this family of molecules accumulated and then disappeared at precise points in the cell cycles of embryonic cells. Evans, T. et al., Cell 33, 389–396. (1983). Cyclin-dependent protein kinase (CDK) activation requires cyclin binding and phosphorylation of a threonine residue by the CDK-activating kinase, CAK. Several recent review articles (Norbury, c. and Nurse, P. A. Rev. Biochem. 61, 441–470 (1992); Nasmyth, K. Curr. Opin. Cell Biol. 5, 166–179 (1993) and Sherr, C. J. Cell 73, 1059–1065 (1993)) detail the regulatory roles which the cyclins and the cyclin dependent kinases play in cell cycle progression.

The criticality of proper cell cycle regulation is intuitive. Disruption of cell cycle regulation leads to uncontrolled cell division. Appreciation of the important roles which cyclins and cyclin dependent kinases play in cell cycle regulation has focused intense research efforts aimed at better understanding cell cycle regulation and then exploiting this knowledge for discovery and development of oncoltyics.

Exploitation of the current knowledge regarding cyclins and CDKs requires experiments involving the addition of appropriate amounts of cyclins and CDKs to allow formation of the desired cyclin-CDK complex for phosphorylation of the conserved threonine residue of the CDK prior to attempting to modulate CDK-mediated phosphorylation of the retinoblastoma protein, Rb. The stochiometric problems inherent in such complicated experimental designs are substantial. The present invention addresses this problem by providing fusion proteins comprising cyclins and CDK4. The biological activities of these fusion proteins eliminates the stochiometry related problems.

SUMMARY OF THE INVENTION

The present invention provides novel fusion proteins comprising cyclins and CDKs. A preferred embodiment of the invention provides fusion proteins comprising human cyclin D1 and human CDK4. The fusion proteins of the invention optionally contain modifications, which facilitate their purification. Addition of histidine residues to selected constructs allows purification via immobilized metal affinity chromatography. Antigenic determinants allowing monoclonal antibody-based affinity chromatography purification are provided in selected embodiments of the invention. Protease cleavage sites are incorporated in selected constructs to allow cleavage of the regions incorporated in the cyclin-CDK fusion proteins for purification. Additional modifications which facilitate purification include strepavadin binding domains and antigenic determinants for antibody affinity chromatography.

DETAILED DESCRIPTION OF THE INVENTION

Figure 1:
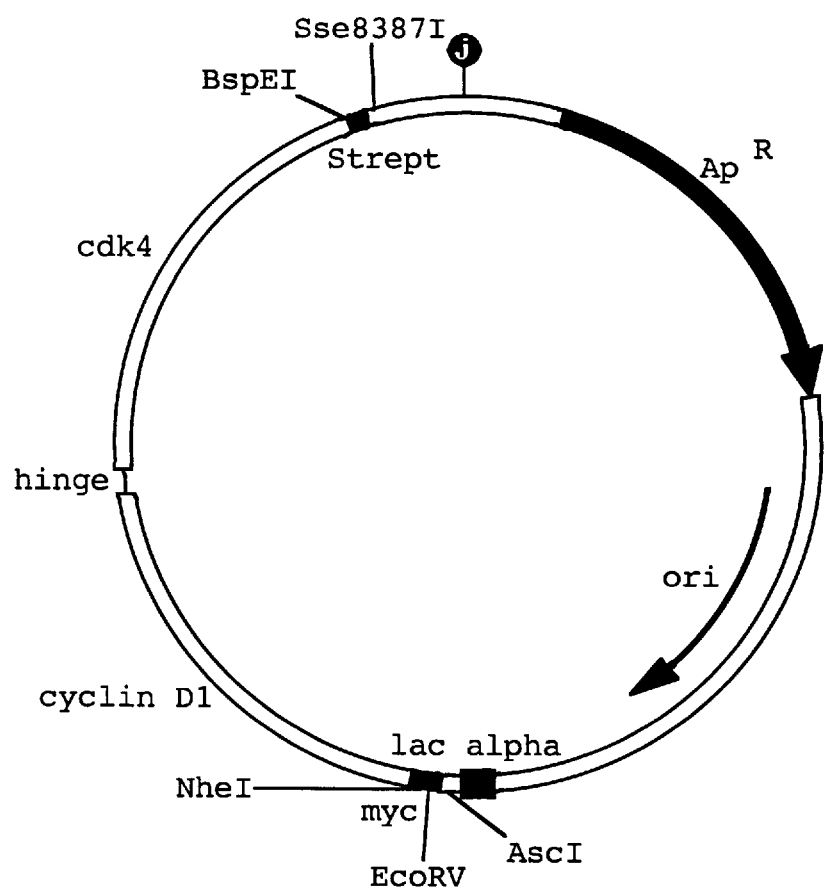
FIG. 1 is a restriction site and function map of plasmid pK415.

The fusion proteins of the present invention comprise cyclins and CDKs linked via various peptide spacers and optionally contain amino acid sequences, which are incorporated to facilitate purification.

The DNA sequence (SEQ ID NO:1) encoding a preferred embodiment of the present invention is provided below.

```
   1 GACGAAAGGG CCTCGTGATA CGCCTATTTT TATAGGTTAA TGTCATGATA
  51 ATAATGGTTT CTTAGACGTC AGGTGGCACT TTTCGGGGAA ATGTGCGCGG
 101 AACCCCTATT TGTTTATTTT TCTAAATACA TTCAAATATG TATCCGCTCA
 151 TGAGACAATA ACCCTGATAA ATGCTTCAAT AATATTGAAA AAGGAAGAGT
 201 ATGAGTATTC AACATTTCCG TGTCGCCCTT ATTCCCTTTT TTGCGGCATT
 251 TTGCCTTCCT GTTTTTGCTC ACCCAGAAAC GCTGGTGAAA GTAAAAGATG
 301 CTGAAGATCA GTTGGGTGCA CGAGTGGGTT ACATCGAACT GGATCTCAAC
 351 AGCGGTAAGA TCCTTGAGAG TTTTCGCCCC GAAGAACGTT TTCCAATGAT
 401 GAGCACTTTT AAAGTTCTGC TATGTGGCGC GGTATTATCC CGTATTGACG
 451 CCGGGCAAGA GCAACTCGGT CGCCGCATAC ACTATTCTCA GAATGACTTG
 501 GTTGAGTACT CACCAGTCAC AGAAAAGCAT CTTACGGATG GCATGACAGT
 551 AAGAGAATTA TGCAGTGCTG CCATAACCAT GAGTGATAAC ACTGCGGCCA
 601 ACTTACTTCT GACAACGATC GGAGGACCGA AGGAGCTAAC CGCTTTTTTG
 651 CACAACATGG GGGATCATGT AACTCGCCTT GATCGTTGGG AACCGGAGCT
 701 GAATGAAGCC ATACCAAACG ACGAGCGTGA CACCACGATG CCTGTAGCAA
 751 TGGCAACAAC GTTGCGCAAA CTATTAACTG GCGAACTACT TACTCTAGCT
 801 TCCCGGCAAC AATTAATAGA CTGGATGGAG GCGGATAAAG TTGCAGGACC
 851 ACTTCTGCGC TCGGCCCTTC CGGCTGGCTG GTTTATTGCT GATAAATCTG
 901 GAGCCGGTGA GCGTGGGTCT CGCGGTATCA TTGCAGCACT GGGGCCAGAT
 951 GGTAAGCCCT CCCGTATCGT AGTTATCTAC ACGACGGGGA GTCAGGCAAC
1001 TATGGATGAA CGAAATAGAC AGATCGCTGA GATAGGTGCC TCACTGATTA
1051 AGCATTGGTA ACTGTCAGAC CAAGTTTACT CATATATACT TTAGATTGAT
1101 TTAAAACTTC ATTTTTAATT TAAAAGGATC TAGGTGAAGA TCCTTTTTGA
1151 TAATCTCATG ACCAAAATCC CTTAACGTGA GTTTTCGTTC CACTGAGCGT
1201 CAGACCCCGT AGAAAAGATC AAAGGATCTT CTTGAGATCC TTTTTTTCTG
1251 CGCGTAATCT GCTGCTTGCA AACAAAAAAA CCACCGCTAC CAGCGGTGGT
1301 TGTTTGCCG  GATCAAGAGC TACCAACTCT TTTTCCGAAG GTAACTGGCT
```

-continued

| | | | | |
|---|---|---|---|---|
| 1351 | TCAGCAGAGC | GCAGATACCA | AATACTGTCC | TTCTAGTGTA | GCCGTAGTTA |
| 1401 | GGCCACCACT | TCAAGAACTC | TGTAGCACCG | CCTACATACC | TCGCTCTGCT |
| 1451 | AATCCTGTTA | CCAGTGGCTG | CTGCCAGTGG | CGATAAGTCG | TGTCTTACCG |
| 1501 | GGTTGGACTC | AAGACGATAG | TTACCGGATA | AGGCGCAGCG | GTCGGGCTGA |
| 1551 | ACGGGGGGTT | CGTGCACACA | GCCCAGCTTG | GAGCGAACGA | CCTACACCGA |
| 1601 | ACTGAGATAC | CTACAGCGTG | AGCATTGAGA | AAGCGCCACG | CTTCCCGAAG |
| 1651 | GGAGAAAGGC | GGACAGGTAT | CCGGTAAGCG | GCAGGGTCGG | AACAGGAGAG |
| 1701 | CGCACGAGGG | AGCTTCCAGG | GGGAAACGCC | TGGTATCTTT | ATAGTCCTGT |
| 1751 | CGGGTTTCGC | CACCTCTGAC | TTGAGCGTCG | ATTTTTGTGA | TGCTCGTCAG |
| 1801 | GGGGGCGGAG | CCTATGGAAA | AACGCCAGCA | ACGCGGCCTT | TTTACGGTTC |
| 1851 | CTGGCCTTTT | GCTGGCCTTT | TGCTCACATG | TTCTTTCCTG | CGTTATCCCC |
| 1901 | TGATTCTGTG | GATAACCGTA | TTACCGCCTT | TGAGTGAGCT | GATACCGCTC |
| 1951 | GCCGCAGCCG | AACGACCGAG | CGCAGCGAGT | CAGTGAGCGA | GGAAGCGGAA |
| 2001 | GAGCGCCCAA | TACGCAAACC | GCCTCTCCCC | GCGCGTTGGC | CGATTCATTA |
| 2051 | ATGCAGCTGG | CACGACAGGT | TTCCCGACTG | GAAAGCGGGC | AGTGAGCGCA |
| 2101 | ACGCAATTAA | TGTGAGTTAG | CTCACTCATT | AGGCACCCCA | GGCTTTACAC |
| 2151 | TTTATGCTTC | CGGCTCGTAT | GTTGTGTGGA | ATTGTGAGCG | GATAACAATT |
| 2201 | TCACACAGGA | AACAGCTATG | ACCATGATTA | CGCCAAGCTT | ACGGCGCGCC |
| 2251 | GCCGCCACCA | TGGCGGAGGA | GCAGAAGCTG | ATATCCGAGG | AGGACCTGCT |
| 2301 | GCTAGCAATG | GAACACCAGC | TCCTGTGCTG | CGAAGTGGAA | ACCATCCGCC |
| 2351 | GCGCGTACCC | CGATGCCAAC | CTCCTCAACG | ACCGGGTGCT | GCGGGCCATG |
| 2401 | CTGAAGGCGG | AGGAGACCTG | CGCGCCCTCG | GTGTCCTACT | TCAAATGTGT |
| 2451 | GCAAAAGGAG | GTCCTGCCGT | CCATGCGGAA | GATCGTCGCC | ACCTGGATGC |
| 2501 | TGGAGGTCTG | CGAGGAACAG | AAGTGCGAGG | AGGAGGTCTT | CCCGCTGGCC |
| 2551 | ATGAACTACC | TGGACGGCTT | CCTGTCCGTG | GAGCCCGTGA | AAAAGAGCCG |
| 2601 | CCTGCAGCTG | CTGGGGGCCA | CTTGCATGTT | CGTGGCCTCT | AAGATGAAGG |
| 2651 | AGACCATCCC | CCTGACGGCC | GAGAAGCTGT | GCATCTACAC | CGACAACTCC |
| 2701 | ATCCGGCCCG | AGGAGCTGCT | GCAAATGGAG | CTGCTCCTGG | TGAACAAGCT |
| 2751 | CAAGTGGAAC | CTGGCCGCAA | TGACCCCGCA | CGATTTCATT | GAACACTTCC |
| 2801 | TCTCCAAAAT | GCCAGAGGCG | GAGGAGAACA | AACAGATCAT | CCGCAAACAC |
| 2851 | GCGCAGACCT | TCGTTGCCCT | CTGTGCCACA | GATGTGAAGT | TCATTTCCAA |
| 2901 | TCCGCCCTCC | ATGGTGGCAG | CGGGGAGCGT | GGTGGCCGCA | GTGCAAGGCC |
| 2951 | TGAACCTGAG | GAGCCCCAAC | AACTTCCTGT | CCTACTACCG | CCTCACACGC |
| 3001 | TTCCTCTCCA | GAGTGATCAA | GTGTGACCCA | GACTGCCTCC | GGGCCTGCCA |
| 3051 | GGAGCAGATC | GAAGCCCTGC | TGGAGTCAAG | CCTGCGCCAG | GCCCAGCAGA |
| 3101 | ACATGGACCC | CAAGGCCGCC | GAGGAGGAGG | AGGAGGAAGA | GGAGGAAGAG |
| 3151 | GAGGTGGACC | TGGCTTGCAC | ACCCACCGAC | GTGCGGGACG | TGGACATCGC |
| 3201 | ATCGAAGGGT | GGTGGAGGTT | CTGGAGGTGG | AGGATCCGGT | GGTGGAGGTT |
| 3251 | CGATGGCTAC | CTCTCGATAT | GAGCCAGTGG | CTGAAATTGG | TGTCGGTGCC |
| 3301 | TATGGGACAG | TGTACAAGGC | CCGTGATCCC | CACAGTGGCC | ACTTTGTGGC |
| 3351 | CCTCAAGAGT | GTGAGAGTCC | CCAATGGAGG | AGGAGGTGGA | GGAGGCCTTC |
| 3401 | CCATCAGCAC | AGTTCGTGAG | GTGGCTTTAC | TGAGGCGACT | GGAGGCTTTT |
| 3451 | GAGCATCCCA | ATGTTGTCCG | GCTGATGGAC | GTCTGTGCCA | CATCCCGAAC |
| 3501 | TGACCGGGAG | ATCAAGGTAA | CCCTGGTGTT | TGAGCATGTA | GACCAGGACC |
| 3551 | TAAGGACATA | TCTGGACAAG | GCACCCCCAC | CAGGCTTGCC | AGCCGAAACG |
| 3601 | ATCAAGGATC | TGATGCGCCA | GTTTCTAAGA | GGCCTAGATT | TCCTTCATGC |
| 3651 | CAATTGCATC | GTTCACCGAG | ATCTGAAGCC | AGAGAACATT | CTGGTGACAA |
| 3701 | GTGGTGGAAC | AGTCAAGCTG | GCTGACTTTG | GCCTGGCCAG | AATCTACAGC |
| 3751 | TACCAGATGG | CACTTACACC | CGTGGTTGTT | ACACTCTGGT | ACCGAGCTCC |
| 3801 | CGAAGTTCTT | CTGCAGTCCA | CATATGCAAC | ACCTGTGGAC | ATGTGGAGTG |
| 3851 | TTGGCTGTAT | CTTTGCAGAG | ATGTTTCGTC | GAAAGCCTCT | CTTCTGTGGA |
| 3901 | AACTCTGAAG | CCGACCAGTT | GGGCAAAATC | TTTGACCTGA | TTGGGCTGCC |
| 3951 | TCCAGAGGAT | GACTGGCCTC | GAGATGTATC | CCTGCCCCGT | GGAGCCTTTC |
| 4001 | CCCCCAGAGG | GCCCCGCCCA | GTGCAGTCGG | TGGTACCTGA | GATGGAGGAG |
| 4051 | TCGGGAGCAC | AGCTGCTGCT | GGAAATGCTG | ACTTTTAACC | CACACAAGCG |
| 4101 | AATCTCTGCC | TTTCGAGCTC | TGCAGCACTC | TTATCTACAT | AAGGATGAAG |
| 4151 | GTAATCCGGA | GGGCGGCAGC | GCTTGGCGCC | ACCCACAGTT | CGGTGGTTGA |
| 4201 | ATAAATAGAT | GAATGACCTG | CAGGTTCACT | GGCCGTCGTT | TTACAACGTC |
| 4251 | GTGACTGGGA | AAACCCTGGC | GTTACCCAAC | TTAATCGCCT | TGCAGCACAT |
| 4301 | CCCCCTTTCG | CCAGCTGGCG | TAATAGCGAA | GAGGCCCGCA | CCGATCGCCC |
| 4351 | TTCCCAACAG | TTGCGCAGCC | TGAATGGCGA | ATGGCGCCTG | ATGCGGTATT |
| 4401 | TTCTCCTTAC | GCATCTGTGC | GGTATTTCAC | ACCGCATATG | GTGCACTCTC |
| 4451 | AGTACAATCT | GCTCTGATGC | CGCATAGTTA | AGCCAGCCCC | GACACCCGCC |
| 4501 | AACACCCGCT | GACGCGCCCT | GACGGGCTTG | TCTGCTCCCG | GCATCCGCTT |
| 4551 | ACAGACAAGC | TGTGACCGTC | TCCGGGAGCT | GCATGTGTCA | GAGGTTTTCA |
| 4601 | CCGTCATCAC | CGAAACGCGC | GA | | |

The polypeptide encoded by SEQ ID NO:1 is presented below as SEQ ID NO:2.

|     |            |            |            |            |            |
|-----|------------|------------|------------|------------|------------|
| 1   | MTMITPSLRR | AAATMAEEQK | LISEEDLLLA | MEHQLLCCEV | ETIRRAYPDA |
| 51  | NLLNDRVLRA | MLKAEETCAP | SVSYFCVQK  | EVLPSMRKIV | ATWMLEVCEE |
| 101 | QKCEEEVFPL | AMNYLDRFLS | LEPVKKSRLQ | LLGATCMFVA | SKMKETIPLT |
| 151 | AEKLCIYTDN | SIRPEELLQM | ELLLVNKLKW | NLAAMTPHDF | IEHFLSKMPE |
| 201 | AEENKQIIRK | HAQTFVALCA | TDVKFISNPP | SMVAAGSVVA | AVQGLNLRSP |
| 251 | NNFLSYYRLT | RFLSRVIKCD | PDCLRACQEQ | IEALLESSLR | QAQQNMDPKA |
| 301 | AEEEEEEEEE | EEVDLACTPT | DVRDVDIASK | GGGGSGGGGS | GGGGSMATSR |
| 351 | YEPVAEIGVG | AYGTVYKARD | PHSGHFVALK | SVRVPNGGGG | GGGLPISTVR |
| 401 | EVALLRRLEA | FEHPNVVRLM | DVCATSRTDR | EIKVTLVFEH | VDQDLRTYLD |
| 451 | KAPPPGLPAE | TIKDLMRQFL | RGLDFLHANC | IVHRDLKPEN | ILVTSGGTVK |
| 501 | LADFGLARIY | SYQMALTPVV | VTLWYRAPEV | LLQSTYATPV | DMWSVGCIFA |
| 551 | EMFRRKPLFC | GNSEADQLGK | IFDLIGLPPE | DDWPRDVSLP | RGAFPPRGPR |
| 601 | PVQSVVPEME | ESGAQLLLEM | LTFNPHKRIS | AFRALQHSYL | HKDEGNPEGG |
| 651 | SAWRHPQFGG |            |            |            |            |

The DNA sequence of SEQ ID NO:1 is the preferred coding sequence for the polypeptide of SEQ ID NO:2. Numerous other DNA sequences will also encode the polypeptide of SEQ ID NO:2 due to the degeneracy of the genetic code. All DNA sequences encoding the polypeptide of SEQ ID NO:2 are contemplated by the present invention and thus are within the scope of the present invention.

The DNA sequence of SEQ ID NO:1 is a component of the plasmid K415. A restriction site and function map of plasmid K415 is provided in FIG. 1. *E. coli* host cells transformed with K415 were deposited in the NRRL, Northern Regional Research Laboratory, 1815 North University Street, Peoria, Ill. 61604 on or before Aug. 9, 1995 and will be available pursuant to Budapest Treaty requirements upon issuance of a patent in a Budapest signatory country. The NRRL accession number for *E. coli*/K415 is B-21490. The routine nature of culturing such organisms, preparing plasmids from the transformants, digesting the plasmids with appropriate restriction endonucleases and isolating the appropriate DNA fragment obviate the need or desirability of discussing these routine steps.

327 correspond to human cyclin D1. Residues 331 through 345 are an illustrative "linker" or polypeptide connector. The terms "linker", "polypeptide connector" and "hinge" are used interchangeably in describing the present invention and all three terms refer to the sequences of amino acids which are used to connect the cyclin and CDK components of the fusion proteins of the present invention. Residues 346 through 648 correspond to human CDK4. Residues 651 through 660 correspond to strepavadin and were engineered into the molecule to allow facile purification.

The polypeptide of SEQ ID NO:2 has numerous components which allow great flexibility in purification, but are not required for the ultimate benefit provided by the present invention-a biologically active fusion protein comprising cyclin and CDK components. A most preferred aspect of this embodiment of the present invention is the cyclin D1-linker-CDK4 component of the molecule. This most preferred aspect is provided below as SEQ ID NO:3.

|     |            |            |            |            |            |
|-----|------------|------------|------------|------------|------------|
| 41  | M E H Q L L C C E V | E T I R R A Y P D A | | | |
| 51  | N L L N D R V L R A | M L K A E E T C A P | S V S Y F K C V Q K | E V L P S M R K I V | A T WM L E V C E E |
| 101 | Q K C E E E V F P L | A M N Y L D R F L S | L E P V K K S R L Q | L L G A T C M F V A | S K M K E T I P L T |
| 151 | A E K L C I Y T D N | S I R P E E L L Q M | E L L L V N K L K W | N L A A M T P H D F | I E H F L S K M P E |
| 201 | A E E N K Q I I R K | H A Q T F V A L C A | T D V K F I S N P P | S M V A A G S V V A | A V Q G L N L R S P |
| 251 | N N F L S Y Y R L T | R F L S R V I K C D | P D C L R A C Q E Q | I E A L L E S S L R | Q A Q Q N M D P K A |
| 301 | A E E E E E E E E E | E E V D L A C T P T | D V R D V D I A S K | G G G G S G G G G S | G G G G S M A T S R |
| 351 | Y E P V A E I G V G | A Y G T V Y K A R D | P H S G H F V A L K | S V R V P N G G G G | G G G L P I S T V R |
| 401 | E V A L L R R L E A | F E H P N V V R L M | D V C A T S R T D R | E I K V T L V F E H | V D Q D L R T Y L D |
| 451 | K A P P P G L P A E | T I K D L M R Q F L | R G L D F L H A N C | I V H R D L K P E N | I L V T S G G T V K |
| 501 | L A D F G L A R I Y | S Y Q M A L T P V V | V L T W Y R A P E V | L L Q S T Y A T P V | D MWS V G C I F A |
| 551 | E M F R R K P L F C | G N S E A D Q L G K | I F D L I G L P P E | D D WP R D V S L P | R G A F P P R G P R |
| 601 | P V Q S V V P E ME | E S G A Q L L L E M | L T F N P H K R I S | A F R A L Q H S Y L | H K D E G N P E |

The distinct functional subcomponents of the polypeptide of SEQ ID NO:2 are described by reference to the amino acid residue numbers provided in SEQ ID NO:2. Residues 18 through 27 comprise the epitope recognized by the monoclonal antibody designated myc. Residues 31 though Biologically active fusion protein comprising a member of the cyclin family and the CDK family are further illustrated by the DNA sequence of SEQ ID NO:4 and the corresponding polypeptide sequence, SEQ ID NO:5. SEQ ID NO:4 is provided immediately below.

```
   1 GACGAAAGGG CCTCGTGATA CGCCTATTTT TATAGGTTAA TGTCATGATA
  51 ATAATGGTTT CTTAGACGTC AGGTGGCACT TTTCGGGGAA ATGTGCGCGG
 101 AACCCCTATT TGTTTATTTT TCTAAATACA TTCAAATATG TATCCGCTCA
 151 TGAGACAATA ACCCTGATAA ATGCTTCAAT AATATTGAAA AAGGAAGAGT
 201 ATGAGTATTC AACATTTCCG TGTCGCCCTT ATTCCCTTTT TTGCGGCATT
 251 TTGCCTTCCT GTTTTTGCTC ACCCAGAAAC GCTGGTGAAA GTAAAAGATG
 301 CTGAAGATCA GTTGGGTGCA CGAGTGGGTT ACATCGAACT GGATCTCAAC
 351 AGCGGTAAGA TCCTTGAGAG TTTTCGCCCC GAAGAACGTT TTCCAATGAT
 401 GAGCACTTTT AAAGTTCTGC TATGTGGCGC GGTATTATCC CGTATTGACG
 451 CCGGGCAAGA GCAACTCGGT CGCCGCATAC ACTATTCTCA GAATGACTTG
 501 GTTGAGTACT CACCAGTCAC AGAAAAGCAT CTTACGGATG CATGACAGT
 551 AAGAGAATTA TGCAGTGCTG CCATAACCAT GAGTGATAAC ACTGCGGCCA
 601 ACTTACTTCT GACAACGATC GGAGGACCGA AGGAGCTAAC CGCTTTTTTG
 651 CACAACATGG GGGATCATGT AACTCGCCTT GATCGTTGGG AACCGGAGCT
 701 GAATGAAGCC ATACCAAACG ACGAGCGTGA CACCACGATG CCTGTAGCAA
 751 TGGCAACAAC GTTGCGCAAA CTATTAACTG GCGAACTACT TACTCTAGCT
 801 TCCCGGCAAC AATTAATAGA CTGGATGGAG GCGGATAAAG TTGCAGGACC
 851 ACTTCTGCGC TCGGCCCTTC CGGCTGGCTG GTTTATTGCT GATAAATCTG
 901 GAGCCGGTGA GCGTGGGTCT CGCGGTATCA TTGCAGCACT GGGGCCAGAT
 951 GGTAAGCCCT CCCGTATCGT AGTTATCTAC ACGACGGGGA GTCAGGCAAC
1001 TATGGATGAA CGAAATAGAC AGATCGCTGA GATAGGTGCC TCACTGATTA
1051 AGCATTGGTA ACTGTCAGAC CAAGTTTACT CATATATACT TTAGATTGAT
1101 TTAAAACTTC ATTTTTAATT TAAAAGGATC TAGGTGAAGA TCCTTTTTGA
1151 TAATCTCATG ACCAAAATCC CTTAACGTGA GTTTTCGTTC CACTGAGCGT
1201 CAGACCCCGT AGAAAAGATC AAAGGATCTT CTTGAGATCC TTTTTTTCTG
1251 CGCGTAATCT GCTGCTTGCA AACAAAAAAA CCACCGCTAC CAGCGGTGGT
1301 TTGTTTGCCG GATCAAGAGC TACCAACTCT TTTTCCGAAG GTAACTGGCT
1351 TCAGCAGAGC GCAGATACCA AATACTGTCC TTCTAGTGTA GCCGTAGTTA
1401 GGCCACCACT TCAAGAACTC TGTAGCACCG CCTACATACC TCGCTCTGCT
1451 AATCCTGTTA CCAGTGGCTG CTGCCAGTGG CGATAAGTCG TGTCTTACCG
1501 GGTTGGACTC AAGACGATAG TTACCGGATA AGGCGCAGCG GTCGGGCTGA
1551 ACGGGGGGTT CGTGCACACA GCCCAGCTTG GAGCGAACGA CCTACACCGA
1601 ACTGAGATAC CTACAGCGTG AGCATTGAGA AAGCGCCACG CTTCCCGAAG
1651 GGAGAAAGGC GGACAGGTAT CCGGTAAGCG GCAGGGTCGG AACAGGAGAG
1701 CGCACGAGGG AGCTTCCAGG GGGAAACGCC TGGTATCTTT ATAGTCCTGT
1751 CGGGTTTCGC CACCTCTGAC TTGAGCGTCG ATTTTTGTGA TGCTCGTCAG
1801 GGGGGCGGAG CCTATGGAAA AACGCCAGCA ACGCGGCCTT TTTACGGTTC
1851 CTGGCCTTTT GCTGGCCTTT TGCTCACATG TTCTTTCCTG CGTTATCCCC
1901 TGATTCTGTG GATAACCGTA TTACCGCCTT TGAGTGAGCT GATACCGCTC
1951 GCCGCAGCCG AACGACCGAG CGCAGCGAGT CAGTGAGCGA GGAAGCGGAA
2001 GAGCGCCCAA TACGCAAACC GCCTCTCCCC GCGCGTTGGC CGATTCATTA
2051 ATGCAGCTGG CACGACAGGT TTCCCGACTG GAAAGCGGGC AGTGAGCGCA
2101 ACGCAATTAA TGTGAGTTAG CTCACTCATT AGGCACCCCA GGCTTTACAC
2151 TTTATGCTTC CGGCTCGTAT GTTGTGTGGA ATTGTGAGCG GATAACAATT
```

-continued

```
2201 TCACACAGGA AACAGCTATG ACCATGATTA CGCCAAGCTT ACGGCGCGCC
2251 GCCGCCACCA TGGCGCATCA TCATCATCAT CATGGAGGTG GAGGTTCGGA
2301 GCAGAAGCTT ATTTCCGAGG AGGATCTGCT GGTGCCACGG GGTTCCCTGC
2351 TAGCAATGGA ACACCAGCTC CTGTGCTGCG AAGTGGAAAC CATCCGCCGC
2401 GCGTACCCCG ATGCCAACCT CCTCAACGAC CGGGTGCTGC GGGCCATGCT
2451 AAAGGCGGAG GAGACCTGCG CGCCCTCGGT GTCCTACTTC AAATGTGTGC
2501 AAAAGGAGGT CCTGCCGTCC ATGCGGAAGA TCGTCGCCAC CTGGATGCTG
2551 GAGGTCTGCG AGGAACAGAA GTGCGAGGAG GAGGTCTTCC CGCTGGCCAT
2601 GAACTACCTG GACCGCTTCC TGTCGCTGGA GCCCGTGAAA AAGAGCCGCC
2651 TGCAGCTGCT GGGGGCCACT TGCATGTTCG TGGCCTCTAA GATGAAGGAG
2701 ACCATCCCCC TGACGGCCGA GAAGCTGTGC ATCTACACCG ACAACTCCAT
2751 CCGGCCCGAG GAGCTGCTGC AAATGGAGCT GCTCCTGGTG AACAAGCTCA
2801 AGTGGAACCT GGCCGCAATG ACCCCGCACG ATTTCATTGA ACACTTCCTC
2851 TCCAAAATGC CAGAGGCGGA GGAGAACAAA CAGATCATCC GCAAACACGC
2901 GCAGACCTTC GTTGCCCTCT GTGCCACAGA TGTGAAGTTC ATTTCCAATC
2951 CGCCCTCCAT GGTGGCAGCG GGGAGCGTGG TGGCCGCAGT GCAAGGCCTG
3001 AACCTGAGGA GCCCCAACAA CTTCCTGTCC TACTACCGCC TCACACGCTT
3051 CCTCTCCAGA GTGATCAAGT GTGACCCAGA CTGCCTCCGG GCCTGCCAGG
3101 AGCAGATCGA AGCCCTGCTG GAGTCAAGCC TGCGCCAGGC CCAGCAGAAC
3151 ATGGACCCCA AGGCCGCCGA GGAGGAGGAG GAGGAAGAGG AGGAAGAGGA
3201 GGTGGACCTG GCTTGCACAC CCACCGACGT GCGGGACGTG GACATCGCAT
3251 CGAAGGGTGG TGGAGGTTCT GGAGGTGGAG GATCCGGTGG TGGAGGTTCG
3301 ATGGCTACCT CTCGATATGA GCCAGTGGCT GAAATTGGTG TCGGTGCCTA
3351 TGGGACAGTG TACAAGGCCC GTGATCCCCA CAGTGGCCAC TTTGTGGCCC
3401 TCAAGAGTGT GAGAGTCCCC AATGGAGGAG GAGGTGGAGG AGGCCTTCCC
3451 ATCAGCACAG TTCGTGAGGT GGCTTTACTG AGGCGACTGG AGGCTTTTGA
3501 GCATCCCAAT GTTGTCCGGC TGATGGACGT CTGTGCCACA TCCCGAACTG
3551 ACCGGGAGAT CAAGGTAACC CTGGTGTTTG AGCATGTAGA CCAGGACCTA
3601 AGGACATATC TGGACAAGGC ACCCCCACCA GGCTTGCCAG CCGAAACGAT
3651 CAAGGATCTG ATGCGCCAGT TTCTAAGAGG CCTAGATTTC CTTCATGCCA
3701 ATTGCATCGT TCACCGAGAT CTGAAGCCAG AGAACATTCT GGTGACAAGT
3751 GGTGGAACAG TCAAGCTGGC TGACTTTGGC CTGGCCAGAA TCTACAGCTA
3801 CCAGATGGCA CTTACACCCG TGGTTGTTAC ACTCTGGTAC CGAGCTCCCG
3851 AAGTTCTTCT GCAGTCCACA TATGCAACAC CTGTGGACAT GTGGAGTGTT
3901 GGCTGTATCT TTGCAGAGAT GTTTCGTCGA AAGCCTCTCT TCTGTGGAAA
3951 CTCTGAAGCC GACCAGTTGG GCAAAATCTT TGACCTGATT GGGCTGCCTC
4001 CAGAGGATGA CTGGCCTCGA GATGTATCCC TGCCCCGTGG AGCCTTTCCC
4051 CCCAGAGGGC CCCGCCCAGT GCAGTCGGTG GTACCTGAGA TGGAGGAGTC
4101 GGGAGCACAG CTGCTGCTGG AAATGCTGAC TTTTAACCCA CACAAGCGAA
4151 TCTCTGCCTT TCGAGCTCTG CAGCACTCTT ATCTACATAA GGATGAAGGT
4201 AATCCGGAGG GCGGCAGCGC TTGGCGCCAC CCACAGTTCG GTGGTTGAAT
4251 AAATAGATGA ATGACCTGCA GGTGCACTCT CAGTACAATC TGCTCTGATG
4301 CCGCATAGTT AAGCCAGCCC CGACACCCGC CAACACCCGC TGACGCGCCC
4351 TGACGGGCTT GTCTGCTCCC GGCATCCGCT TACAGACAAG CTGTGACCGT
```

-continued
```
4401 CTCCGGGAGC TGCATGTGTC AGAGGTTTTC ACCGTCATCA CCGAAACGCG

4451 CGA
```

The polypeptide encoded by the sequence of SEQ ID NO:4 is provided below as SEQ ID NO:5.

```
  1 MAHHHHHHGG  GGSEQKLISE  EDLLVPRGSL  LAMEHQLLCC  EVETIRRAYP

51 DANLLNDRVL  RAMLKAEETC  APSVSYFKCV  QKEVLPSMRK  IVATWMLEVC

101 EEQKCEEEVF  PLAMNYLDRF  LSLEPVKKSR  LQLLGATCMF  VASKMKETIP

151 LTAEKLCIYT  DNSIRPEELL  QMELLLVNKL  KWNLAAMTPH  DFIEHFLSKM

201 PEAEENKQII  RKHAQTFVAL  CATDVKFISN  PPSMVAAGSV  VAAVQGLNLR

251 SPNNFLSYYR  LTRFLSRVIK  CDPDCLRACQ  EQIEALLESS  LRQAQQNMDP

301 KAAEEEEEEE  EEEEVDLACT  PTDVRDVDIA  SKGGGGSGGG  GSGGGGSMAT

351 SRYEPVAEIG  VGAYGTVYKA  RDPHSGHFVA  LKSVRVPNGG  GGGGGLPIST

401 VREVALLRRL  EAFEHPNVVR  LMDVCATSRT  DREIKVTLVF  EHVDQDLRTY

451 LDKAPPPGLP  AETIKDLMRQ  FLRGLDFLHA  NCIVHRDLKP  ENILVTSGGT

501 VKLADFGLAR  IYSYQMALTP  VVVTLWYRAP  EVLLQSTYAT  PVDMWSVGCI

551 FAEMFRRKPL  FCGNSEADQL  GKIFDLIGLP  PEDDWPRDVS  LPRGAFPPRG

601 PRPVQSVVPE  MEESGAQLLL  EMLTFNPHKR  ISAFRALQHS  YLHKDEGNPE

651 GGSAWRHPQF  GG
```

The DNA sequence of SEQ ID NO:4 is the p referred coding sequence for the polypeptide of SEQ ID NO:5. Numerous other DNA sequences will also encode the polypeptide of SEQ ID NO:4 due to the degeneracy of the genetic code. All DNA sequences encoding the polypeptide of SEQ ID NO:5 are contemplated by the present invention and thus are within the scope of the present invention.

Figure 2:
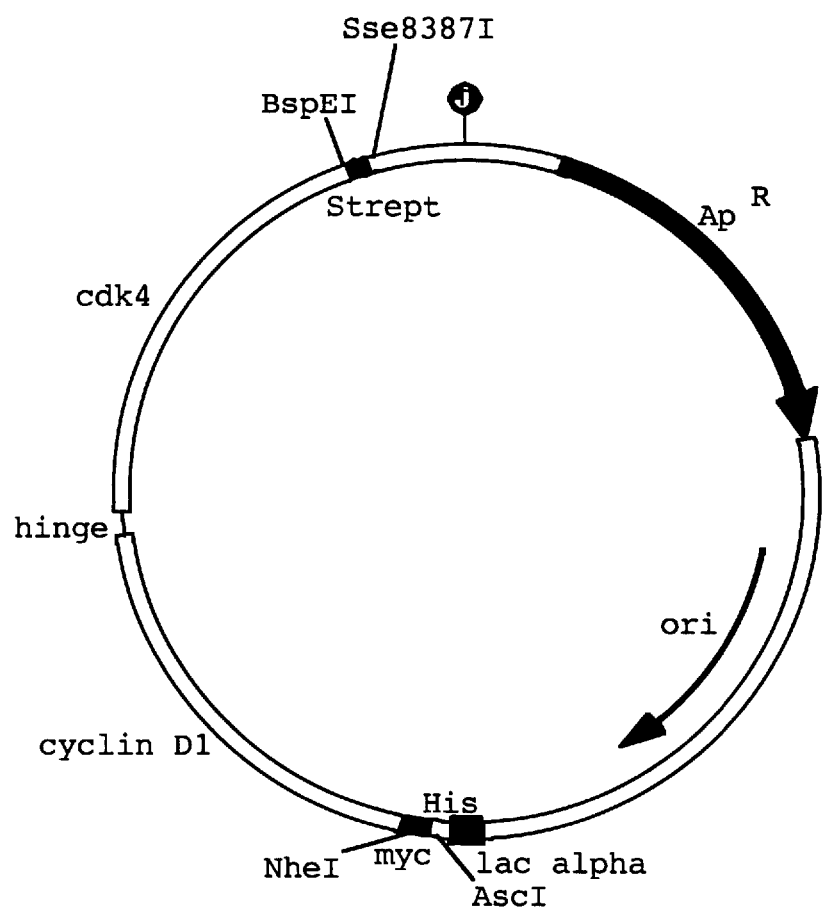
FIG. 2 is a restriction site and function map of plasmid pK485.

The DNA sequence of SEQ ID NO:4 is a component of the plasmid K485. A restriction site and function map of plasmid K485 is provided in FIG. 2. E. coli host cells transformed with K485 were deposited in the NRRL, Northern Regional Research Laboratory, 1815 North University Street, Peoria, Ill. 61604 on or before Aug. 9, 1995 and will be available pursuant to Budapest Treaty requirements upon issuance of a patent in a Budapest signatory country. The NRRL accession number for E. coli/K485 is B-21492. The routine nature of culturing such organisms, preparing plasmids from the transformants, digesting the plasmids with appropriate restriction endonucleases and isolating the appropriate DNA fragment obviate the need or desirability of discussing these routine steps.

The DNA sequence of Sequence ID 4 and the polypeptide encoded thereby comprise human cyclin D1 and human CDK4 which are joined by a polypeptide linker. The distinct functional subcomponents of the polypeptide of SEQ ID NO:5 are described by reference to the amino acid residue numbers provided in SEQ ID NO:5. Amino acid residues 2 through 8 are Histidine residues which were incorporated to allow immobilized metal affinity chromatography purification. Residues 14 through 23 contain the antigenic determinant recognized by the myc monoclonal antibody and thereby allow myc monoclonal antibody based affinity purification. Residues 24 through 28 contain a thrombin cleavage site and were engineered into the polypeptide of SEQ ID NO:5 to allow cleavage of the molecule on the amino side of the human cyclin D1 component. Residues 43 through 329 correspond to human cyclin D1. Residues 333 through 347 are the polypeptide linker used to join the human cyclin D1 and human CDK4 components of the molecule. Residues 348 through 650 correspond to human CDK4. Residues 653 through 662 were engineered into the molecule to provide a sequence which binds to paramagnetic streptavadin beads and thus allows facile purification of the molecule.

The present invention also provides the DNA sequence of SEQ ID NO:6, which is presented below.

```
  1 GACGAAAGGG  CCTCGTGATA  CGCCTATTTT  TATAGGTTAA  TGTCATGATA

51 ATAATGGTTT  CTTAGACGTC  AGGTGGCACT  TTTCGGGGAA  ATGTGCGCGG

101 AACCCCTATT  TGTTTATTTT  TCTAAATACA  TTCAAATATG  TATCCGCTCA

151 TGAGACAATA  ACCCTGATAA  ATGCTTCAAT  AATATTGAAA  AAGGAAGAGT

201 ATGAGTATTC  AACATTTCCG  TGTCGCCCTT  ATTCCCTTTT  TTGCGGCATT
```

```
 251 TTGCCTTCCT GTTTTTGCTC ACCCAGAAAC GCTGGTGAAA GTAAAAGATG
 301 CTGAAGATCA GTTGGGTGCA CGAGTGGGTT ACATCGAACT GGATCTCAAC
 351 AGCGGTAAGA TCCTTGAGAG TTTTCGCCCC GAAGAACGTT TTCCAATGAT
 401 GAGCACTTTT AAAGTTCTGC TATGTGGCGC GGTATTATCC CGTATTGACG
 451 CCGGGCAAGA GCAACTCGGT CGCCGCATAC ACTATTCTCA GAATGACTTG
 501 GTTGAGTACT CACCAGTCAC AGAAAAGCAT CTTACGGATG GCATGACAGT
 551 AAGAGAATTA TGCAGTGCTG CCATAACCAT GAGTGATAAC ACTGCGGCCA
 601 ACTTACTTCT GACAACGATC GGAGGACCGA AGGAGCTAAC CGCTTTTTTG
 651 CACAACATGG GGGATCATGT AACTCGCCTT GATCGTTGGG AACCGGAGCT
 701 GAATGAAGCC ATACCAAACG ACGAGCGTGA CACCACGATG CCTGTAGCAA
 751 TGGCAACAAC GTTGCGCAAA CTATTAACTG GCGAACTACT TACTCTAGCT
 801 TCCCGGCAAC AATTAATAGA CTGGATGGAG GCGGATAAAG TTGCAGGACC
 851 ACTTCTGCGC TCGGCCCTTC CGGCTGGCTG GTTTATTGCT GATAAATCTG
 901 GAGCCGGTGA GCGTGGGTCT CGCGGTATCA TTGCAGCACT GGGGCCAGAT
 951 GGTAAGCCCT CCCGTATCGT AGTTATCTAC ACGACGGGGA GTCAGGCAAC
1001 TATGGATGAA CGAAATAGAC AGATCGCTGA GATAGGTGCC TCACTGATTA
1051 AGCATTGGTA ACTGTCAGAC CAAGTTTACT CATATATACT TTAGATTGAT
1101 TTAAAACTTC ATTTTTAATT TAAAAGGATC TAGGTGAAGA TCCTTTTTGA
1151 TAATCTCATG ACCAAAATCC CTTAACGTGA GTTTTCGTTC CACTGAGCGT
1201 CAGACCCCGT AGAAAAGATC AAAGGATCTT CTTGAGATCC TTTTTTTCTG
1251 CGCGTAATCT GCTGCTTGCA AACAAAAAAA CCACCGCTAC CAGCGGTGGT
1301 TTGTTTGCCG GATCAAGAGC TACCAACTCT TTTTCCGAAG GTAACTGGCT
1351 TCAGCAGAGC GCAGATACCA AATACTGTCC TTCTAGTGTA GCCGTAGTTA
1401 GGCCACCACT TCAAGAACTC TGTAGCACCG CCTACATACC TCGCTCTGCT
1451 AATCCTGTTA CCAGTGGCTG CTGCCAGTGG CGATAAGTCG TGTCTTACCG
1501 GGTTGGACTC AAGACGATAG TTACCGGATA AGGCGCAGCG GTCGGGCTGA
1551 ACGGGGGGTT CGTGCACACA GCCCAGCTTG GAGCGAACGA CCTACACCGA
1601 ACTGAGATAC CTACAGCGTG AGCATTGAGA AAGCGCCACG CTTCCCGAAG
1651 GGAGAAAGGC GGACAGGTAT CCGGTAAGCG GCAGGGTCGG AACAGGAGAG
1701 CGCACGAGGG AGCTTCCAGG GGGAAACGCC TGGTATCTTT ATAGTCCTGT
1751 CGGGTTTCGC CACCTCTGAC TTGAGCGTCG ATTTTTGTGA TGCTCGTCAG
1801 GGGGGCGGAG CCTATGGAAA AACGCCAGCA ACGCGGCCTT TTTACGGTTC
1851 CTGGCCTTTT GCTGGCCTTT TGCTCACATG TTCTTTCCTG CGTTATCCCC
1901 TGATTCTGTG GATAACCGTA TTACCGCCTT TGAGTGAGCT GATACCGCTC
1951 GCCGCAGCCG AACGACCGAG CGCAGCGAGT CAGTGAGCGA GGAAGCGGAA
2001 GAGCGCCCAA TACGCAAACC GCCTCTCCCC GCGCGTTGGC CGATTCATTA
2051 ATGCAGCTGG CACGACAGGT TTCCCGACTG GAAAGCGGGC AGTGAGCGCA
2101 ACGCAATTAA TGTGAGTTAG CTCACTCATT AGGCACCCCA GGCTTTACAC
2151 TTTATGCTTC CGGCTCGTAT GTTGTGTGGA ATTGTGAGCG GATAACAATT
2201 TCACACAGGA AACAGCTATG ACCATGATTA CGCCAAGCTT ACGGCGCGCC
2251 GCCGCCACCA TGGCGCATCA TCATCATCAT CATGGAGGTG GAGGTTCGGA
2301 GCAGAAGCTT ATTTCCGAGG AGGATCTGCT GGTGCCACGC GGTTCCCTGC
2351 TAGCAATGGA ACACCAGCTC CTGTGCTGCG AAGTGGAAAC CATCCGCCGC
2401 GCGTACCCCG ATGCCAACCT CCTCAACGAC CGGGTGCTGC GGGCCATGCT
```

-continued
```
2451 AAAGGCGGAG GAGACCTGCG CGCCCTCGGT GTCCTACTTC AAATGTGTGC
2501 AAAAGGAGGT CCTGCCGTCC ATGCGGAAGA TCGTCGCCAC CTGGATGCTG
2551 GAGGTCTGCG AGGAACAGAA GTGCGAGGAG GAGGTCTTCC CGCTGGCCAT
2601 GAACTACCTG GACCGCTTCC TGTCGCTGGA GCCCGTGAAA AAGAGCCGCC
2651 TGCAGCTGCT GGGGGCCACT TGCATGTTCG TGGCCTCTAA GATGAAGGAG
2701 ACCATCCCCC TGACGGCCGA GAAGCTGTGC ATCTACACCG ACAACTCCAT
2751 CCGGCCCGAG GAGCTGCTGC AAATGGAGCT GCTCCTGGTG AACAAGCTCA
2801 AGTGGAACCT GGCCGCAATG ACCCCGCACG ATTTCATTGA ACACTTCCTC
2851 TCCAAAATGC AGAGGCGGA GGAGAACAAA CAGATCATCC GCAAACACGC
2901 GCAGACCTTC GTTGCCCTCT GTGCCACAGA TGTGAAGTTC ATTTCCAATC
2951 CGCCCTCCAT GGTGGCAGCG GGGAGCGTGG TGGCCGCAGT GCAAGGCCTG
3001 AACCTGAGGA GCCCCAACAA CTTCCTGTCC TACTACCGCC TCACACGCTT
3051 CCTCTCCAGA GTGATCAAGT GTGACCCAGA CTGCCTCCGG GCCTGCCAGG
3101 AGCAGATCGA AGCCCTGCTG GAGTCAAGCC TGCGCCAGGC CCAGCAGAAC
3151 ATGGACCCCA AGGCCGCCGA GGAGGAGGAG GAGGAAGAGG AGGAAGAGGA
3201 GGTGGACCTG GCTTGCACAC CCACCGACGT GCGGGACGTG GACATCGCAT
3251 CGATGGGTGG AGGTTCTGGT GGAGGTTCTG GTGGAGGTTC TGGTGGAGGT
3301 TCTGGTGGAG GTTCTGGTGG AGGTTCTGGC TTAAGTTCGA AGGGTGGTGG
3351 AGGTTCTGGA GGTGGAGGAT CCGGTGGTGG AGGTTCGATG GCTACCTCTC
3401 GATATGAGCC AGTGGCTGAA ATTGGTGTCG GTGCCTATGG GACAGTGTAC
3451 AAGGCCCGTG ATCCCCACAG TGGCCACTTT GTGGCCCTCA AGAGTGTGAG
3501 AGTCCCCAAT GGAGGAGGAG GTGGAGGAGG CCTTCCCATC AGCACAGTTC
3551 GTGAGGTGGC TTTACTGAGG CGACTGGAGG CTTTTGAGCA TCCCAATGTT
3601 GTCCGGCTGA TGGACGTCTG TGCCACATCC CGAACTGACC GGGAGATCAA
3651 GGTAACCCTG GTGTTTGAGC ATGTAGACCA GGACCTAAGG ACATATCTGG
3701 ACAAGGCACC CCCACCAGGC TTGCCAGCCG AAACGATCAA GGATCTGATG
3751 CGCCAGTTTC TAAGAGGCCT AGATTTCCTT CATGCCAATT GCATCGTTCA
3801 CCGAGATCTG AAGCCAGAGA ACATTCTGGT GACAAGTGGT GGAACAGTCA
3851 AGCTGGCTGA CTTTGGCCTG GCCAGAATCT ACAGCTACCA GATGGCACTT
3901 ACACCCGTGG TTGTTACACT CTGGTACCGA GCTCCCGAAG TTCTTCTGCA
3951 GTCCACATAT GCAACACCTG TGGACATGTG GAGTGTTGGC TGTATCTTTG
4001 CAGAGATGTT TCGTCGAAAG CCTCTCTTCT GTGGAAACTC TGAAGCCGAC
4051 CAGTTGGGCA AAATCTTTGA CCTGATTGGG CTGCCTCCAG AGGATGACTG
4101 GCCTCGAGAT GTATCCCTGC CCCGTGGAGC CTTTCCCCCC AGAGGGCCCC
4151 GCCCAGTGCA GTCGGTGGTA CCTGAGATGG AGGAGTCGGG AGCACAGCTG
4201 CTGCTGGAAA TGCTGACTTT TAACCCACAC AAGCGAATCT CTGCCTTTCG
4251 AGCTCTGCAG CACTCTTATC TACATAAGGA TGAAGGTAAT CCGGAGGGCG
4301 GCAGCGCTTG GCGCCACCCA CAGTTCGGTG GTTGAATAAA TAGATGAATG
4351 ACCTGCAGGT GCACTCTCAG TACAATCTGC TCTGATGCCG CATAGTTAAG
4401 CCAGCCCCGA CACCCGCCAA CACCCGCTGA CGCGCCCTGA CGGGCTTGTC
4451 TGCTCCCGGC ATCCGCTTAC AGACAAGCTG TGACCGTCTC CGGGAGCTGC
4501 ATGTGTCAGA GGTTTTCACC GTCATCACCG AAACGCGCGA
```

The polypeptide encoded by SEQ ID NO:6 is presented below as SEQ ID NO:7.

```
  1 MT MI T P S L R R  A A A T M A H H H H  H H G G G G S E Q K  L I S E E D L L V P  R G S L L A M E H Q
 51 L L C C E V E T I R  R A Y P D A N L L N  D R V L R A M L K A  E E T C A P S V S Y  F K C V Q K E V L P
101 S MR K I V A T WM  L E V C E E Q K C E  E E V F P L A M N Y  L D R F L S L E P V  K K S R L Q L L G A
151 T C MF V A S K MK  E T I P L T A E K L  C I Y T D N S I R P  E E L L Q M E L L L  V N K L K W N L A A
201 MT P H D F I E H F  L S K M P E A E E N  K Q I I R K H A Q T  F V A L C A T D V K  F I S N P P S M V A
251 A G S V V A A V Q G  L N L R S P N N F L  S Y Y R L T R F L S  R V I K C D P D C L  R A C Q E Q I E A L
301 L E S S L R Q A Q Q  N M D P K A A E E E  E E E E E E E E V D  L A C T P T D V R D  V D I A S M G G G S
351 G G G S G G G S G G  G S G G G S G G G S  G L S S K G G G G S  G G G G S G G G G S  M A T S R Y E P V A
401 E I G V G A Y G T V  Y K A R D P H S G H  F V A L K S V R V P  N G G G G G G G L P  I S T V R E V A L L
451 R R L E A F E H P N  V V R L M D V C A T  S R T D R E I K V T  L V F E H V D Q D L  R T Y L D K A P P P
501 G L P A E T I K D L  M R Q F L R G L D F  L H A N C I V H R D  L K P E N I L V T S  G G T V K L A D F G
551 L A R I Y S Y Q M A  L T P V V V T L W Y  R A P E V L L Q S T  Y A T P V D M W S V  G C I F A E M F R R
601 K P L F C G N S E A  D Q L G K I F D L I  G L P P E D D W P R  D V S L P R G A F P  P R G P R P V Q S V
651 V P E M E E S G A Q  L L L E M L T F N P  H K R I S A F R A L  Q H S Y L H K D E G  N P E G G S A W R H
701 P Q F G G
```

The DNA sequence of SEQ ID NO:6 is the preferred coding sequence for the polypeptide of SEQ ID NO:7. Numerous other DNA sequences will also encode the polypeptide of SEQ ID NO:6 due to the degeneracy of the genetic code. All DNA sequences encoding the polypeptide of SEQ ID NO:7 are contemplated by the present invention and thus are within the scope of the present invention.

Figure 3:
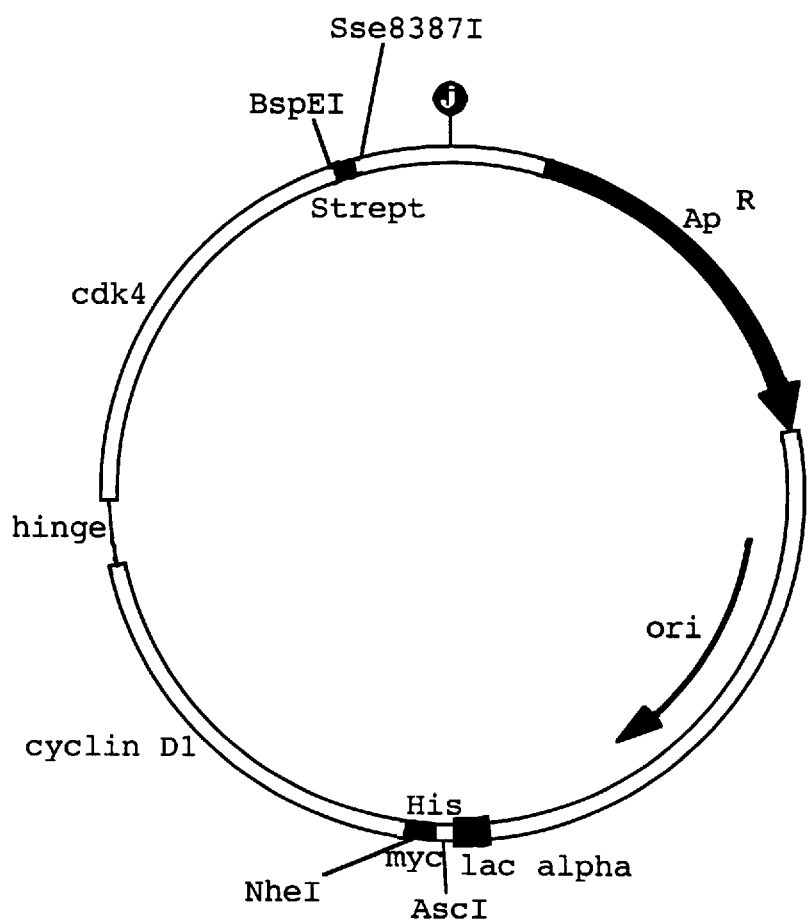
FIG. 3 is a restriction site and function map of plasmid pK480.

The DNA sequence of SEQ ID NO:6 is a component of the plasmid K480. A restriction site and function map of plasmid K480 is provided in FIG. 3. *E. coli* host cells transformed with K480 were deposited in the NRRL, Northern Regional Research Laboratory, 1815 North University Street, Peoria, Ill. 61604 on or before Aug. 9, 1995 and will be available pursuant to Budapest Treaty requirements upon issuance of a patent in a Budapest signatory country. The NRRL accession number for *E. coli*/K480 is B-21491. The routine nature of culturing such organisms, preparing plasmids from the transformants, digesting the plasmids with appropriate restriction endonucleases and isolating the appropriate DNA fragment obviate the need or desirability of discussing these routine steps.

The DNA sequence of SEQ ID NO:6 and the polypeptide encoded thereby comprise human cyclin D1 and human CDK4 which are joined by a polypeptide linker. The distinct functional subcomponents of the polypeptide of SEQ ID NO:7 are described by reference to the amino acid residue numbers provided in SEQ ID NO:7. Amino acid residues 17 through 22 are Histidine residues which were incorporated to allow immobilized metal affinity chromatography purification. Residues 28 through 37 contain the antigenic determinant recognized by the myc monoclonal antibody and thereby allow myc monoclonal antibody based affinity purification. Residues 38 through 43 contain a thrombin cleavage site and were engineered into the polypeptide of Sequence ID 7 to allow cleavage of the molecule on the amino side of the human cyclin D1 component. Residues 47 through 343 correspond to human cyclin D1. Residues 347 through 390 are the polypeptide linker used to join the human cyclin D1 and human CDK4 components of the molecule. Residues 391 through 693 correspond to human CDK4. Residues 696 through 705 were engineered into the molecule to provide a sequence which binds to paramagnetic streptavadin beads and thus allows facile purification of the molecule.

The molecule of SEQ ID NO:7 shares several features with the molecules of SEQ ID NOs: 2 and 5. The polypeptide linker which joins the human cyclin D1 and the human CDK4 portions of the molecule of SEQ ID NO:7 is substantially different from the polypeptide linkers of the molecules of SEQ ID NOs 2 and 5. The structural dissimilarity of the linkers combined with the biological activity of the fusion proteins of the invention underscores the flexibility in linker selection. Accordingly, the fusion proteins of the present invention are not limited to cyclin-CDK fusion proteins containing the linkers which are specifically exemplified.

The fusion protein of SEQ ID NO:7 has the additional features discussed above for allowing great flexibility in choice of purification schemes. The preferred aspect of this embodiment of the present invention is the segment of the molecule comprising the biologically active human cyclin D1-linker-human CDK4 sequence. This preferred sequence is set forth below as SEQ ID NO:8.

```
 47                                                                                            M E H Q
 51 L L C C E V E T I R  R A Y P D A N L L N  D R V L R A M L K A  E E T C A P S V S Y  F K C V Q K E V L P
101 S MR K I V A T WM  L E V C E E Q K C E  E E V F P L A M N Y  L D R F L S L E P V  K K S R L Q L L G A
```

```
151 T C MF V A S K MK   E T I P L T A E K L   C I YT D N S I R P   E E L L Q ME L L L   V N K L K W N L A A
201 MT P H D F I E HF   L S K MP E A E E N   K Q I I R K H A Q T   F V A L C A T D V K   F I S N P P S MV A
251 A G S V V A A V Q G   L N L R S P N N F L   S Y Y R L T R F L S   R V I K C D P D C L   R A C Q E Q I E A L
301 L E S S L R Q A Q Q   N M D P K A A E E E   E E E E E E E E V D   L A C T P T D V R D   V D I A S M G G G S
351 G G G S G G G S G G   G S G G G S G G G S   G L S S K G G G G S   G G G G S G G G G S   M A T S R Y E P V A
401 E I G V G A Y G T V   Y K A R D P H S G H   F V A L K S V R V P   N G G G G G G G L P   I S T V R E V A L L
451 R R L E A F E H P N   V V R L M D V C A T   S R T D R E I K V T   L V F E H V D Q D L   R T Y L D K A P P P
501 G L P A E T I K D L   M R Q F L R G L D F   L H A N C I V H R D   L K P E N I L V T S   G G T V K L A D F G
551 L A R I Y S Y Q M A   L T P V V V T L W Y   R A P E V L L Q S T   Y A T P V D M W S V   G C I F A E M F R R
601 K P L F C G N S E A   D Q L G K I F D L I   G L P P E D D W P R   D V S L P R G A F P   P R G P R P V Q S V
651 V P E M E E S G A Q   L L L E M L T F N P   H K R I S A F R A L   Q H S Y L H K D E G   N P E
```

Skilled artisans will recognize that the proteins of the present invention can be synthesized by a number of different methods. All of the amino acid compounds of the invention can be made by chemical methods well known in the art, including solid phase peptide synthesis, or recombinant methods. Both methods are described in U.S. Pat. No. 4,617,149, herein incorporated by reference.

The principles of solid phase chemical synthesis of polypeptides are well known in the art and may be found in general texts in the area. See, e.g., H. Dugas and C. Penney, BIOORGANIC CHEMISTRY, (1981) Springer-Verlag, New York, pgs. 54–92. For examples, peptides may be synthesized by solid-phase methodology utilizing an Applied Biosystems 430A peptide synthesizer (commercially available from Applied Biosystems, Foster City Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. The following side chain protection may be used:

Arg, Tosyl
Asp, cyclohexyl
Glu, cyclohexyl
Ser, Benzyl
Thr, Benzyl
Tyr, 4-bromo carbobenzoxy Removal of the t-butoxycarbonyl moiety (deprotection) may be accomplished with trifluoroacetic acid (TFA) in methylene chloride. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees centigrade or below, preferably −20° C. for thirty minutes followed by thirty minutes at 0° C.

After removal of the hydrogen fluoride, the peptide/resin is washed with ether, and the peptide extracted with glacial acetic acid and then lyophilized. Purification is accomplished by size-exclusion chromatography on a Sephadex G-10 (Pharmacia) column in 10% acetic acid.

The proteins of the present invention may also be produced by recombinant methods. Recombinant methods are preferred if a high yield is desired. A general method for the construction of any desired DNA sequence is provided in J. Brown, et al., Methods in Enzymology, 68:109 (1979). See also, J. Sambrook, et al., supra.

The basic steps in the recombinant production of desired proteins are:

a) construction of a synthetic or semi-synthetic DNA encoding the protein of interest;

b) integrating said DNA into an expression vector in a manner suitable for the expression of the protein of interest, either alone or as a fusion protein;

c) transforming an appropriate eukaryotic or prokaryotic host cell with said expression vector, d) culturing said transformed or transfected host cell in a manner to express the protein of interest; and e) recovering and purifying the recombinantly produced protein of interest.

In general, prokaryotes are used for cloning of DNA sequences in constructing the vectors of this invention. Prokaryotes may also be employed in the production of the protein of interest. For example, the *Escherichia coli* K12 strain 294 (ATCC No. 31446) is particularly useful for the prokaryotic expression of foreign proteins. A commercially available *E. coli* strain which is preferred for prokaryotic expression of the fusion proteins of the invention is designated DH10B. DH10B is available from Gibco BRL, P.O. Box 68, Grand Island, N.Y. 14072-0068. Other strains of *E coli* which may be used (and their relevant genotypes) include the following.

Strain Genotype

DH5a F$^-$ ($\phi$80dlacZDM15), D(lacZYA-argF)U169 supE44, hsdR17 ($r_K^-$, $m_K^+$), recA1, endA1, gyrA96, thi-1, relA1

HB101 supE44, hsdS20 ($r_B^-$, $m_B^-$), recA13, ara-14, proA2 lacY1, galK2, rpsL20, xyl-5, mtl-1, mcrB, mrr JM109 recA1, e14$^-$(mcrA). supE44, endA1, hsdR17 ($r_K^-$, $m_k^+$), gyrA96, relA1, thi-1, $\Delta$(lac-proAB), F'[traD36, proAB+ lacI$^q$, lacZ$\Delta$M15]

RR1 supE44, hsdS20 ($r_B^-$ $m_B^-$), ara-14 proA2, lacY1, galk2, rpsL20, xyl-5, mtl-5 chi1776 F$^-$, ton, A53, dapD8, minA1, supE42 (glnV42), D(gal-uvrB)40, minB2, rfb-2, gyrA25, thyA142, oms-2, metC65, oms-1, B(bioH-asd)29, cycB2, cycA1, hsdR2

294 endA, thi⁻, hsr⁻, hsm$_k^+$ (U.S. Pat. No. 4,366,246)

LE392 F⁻, hsdR514 (r⁻m⁻), supE44, supF58, lacY1, galk2, galT22, metB1, trpR55

These strains are all commercially available from suppliers such as: Bethesda Research Laboratories, Gaithersburg, Md. 20877 and Stratagene Cloning Systems, La Jolla, Calif. 92037; or are readily available to the public from sources such as the American Type Culture Collection, 12301 Parklawn Drive, Rockville, Md., 10852-1776.

Except where otherwise noted, these bacterial strains can be used interchangeably. The genotypes listed are illustrative of many of the desired characteristics for choosing a bacterial host and are not meant to limit the invention in any way. The genotype designations are in accordance with standard nomenclature. See, for example, J. Sambrook, et al., supra. A preferred strain of *E. coli* employed in the cloning and expression of the genes of this invention is RV308, which is available from the ATCC under accession number ATCC 31608, and is described in U.S. Pat. No. 4,551,433, issued Nov. 5, 1985. The three *E. coli* host cells transformed with the vectors described in FIGS. 1, 2 and 3 and discussed in preceding sections will be publicly available upon issuance of a patent in a "Budapest Treaty" country and thus are the preferred means for prokaryotic expression of the fusion proteins which are described herein as illustrative of the fusion proteins of the invention. The fusion proteins produced by the *E. coli* "deposits" of the invention require solubilization, folding and phosphorylation for complete biological activity. While they are still preferred when substantial amounts of fusion protein are desired, the facile nature of numerous eukaryotic expression systems results in a preference for these systems when modest amounts of the biologically active fusion proteins are desired.

In addition to the strains of *E. coli* discussed supra, bacilli such as *Bacillus subtilis*, other enterobacteriaceae such as *Salmonella typhimurium* or *Serratia marcescans*, and various Pseudomonas species may also be used. In addition to these gram-negative bacteria, other bacteria, especially Streptomyces, spp., may be employed in the prokaryotic cloning and expression of the proteins of this invention.

Promoters suitable for use with prokaryotic hosts include the b-lactamase [vector pGX2907 (ATCC 39344) contains the replicon and b-lactamase gene] and lactose promoter systems [Chang et al., *Nature* (*London*), 275:615 (1978); and Goeddel et al., *Nature* (*London*), 281:544 (1979)], alkaline phosphatase, the tryptophan (trp) promoter system [vector pATH1 (ATCC 37695) is designed to facilitate expression of an open reading frame as a trpE fusion protein under control of the trp promoter] and hybrid promoters such as the tac promoter (isolatable from plasmid pDR540 ATCC-37282). However, other functional bacterial promoters, whose nucleotide sequences are generally known, enable one of skill in the art to ligate them to DNA encoding the proteins of the instant invention using linkers or adapters to supply any required restriction sites. Promoters for use in bacterial systems will also contain a Shine-Dalgarno sequence operably linked to the DNA encoding the desired polypeptides. These examples are illustrative rather than limiting.

The proteins of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein of interest. A variety of peptidases (e.g. trypsin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13 in PROTEIN PURIFICATION: FROM MOLECULAR MECHANISMS TO LARGE SCALE PROCESSES, American Chemical Society, Washington, D.C. (1990).

In addition to cloning and expressing the genes of interest in the prokaryotic systems discussed above, the proteins of the present invention may also be produced in eukaryotic systems. The present invention is not limited to use in a particular eukaryotic host cell. A variety of eukaryotic host cells are available from depositories such as the American Type Culture Collection (ATCC) and are suitable for use with the vectors of the present invention. The choice of a particular host cell depends to some extent on the particular expression vector used to drive expression of the cyclin-CDK fusion protein-encoding nucleic acids of the present invention. Exemplary host cells suitable for use in the present invention are listed in Table I

TABLE I

| Host Cell | Origin | Source |
| --- | --- | --- |
| HepG-2 | Human Liver Hepatoblastoma | ATCC HB 8065 |
| CV-1 | African Green Monkey Kidney | ATCC CCL 70 |
| LLC-MK$_2$ | Rhesus Monkey Kidney | ATCC CCL 7 |
| 3T3 | Mouse Embryo Fibroblasts | ATCC CCL 92 |
| CHO-K1 | Chinese Hamster Ovary | ATCC CCL 61 |
| HeLa | Human Cervix Epitheloid | ATCC CCL 2 |
| RPMI8226 | Human Myeloma | ATCC CCL 155 |
| H4IIEC3 | Rat Hepatoma | ATCC CCL 1600 |
| C127I | Mouse Fibroblast | ATCC CCL 1616 |
| 293 | Human Embyronal Kidney | ATCC CRL 1573 |
| HS-Sultan | Human Plasma Cell Plasmocytoma | ATCC CCL 1484 |
| BHK-21 | Baby Hamster Kidney | ATCC CCL 10 |

A preferred eukaryotic cell line of use in expressing the fusion proteins of this invention is the widely available cell line AV12-664 (hereinafter "AV12"). This cell line is available from the American Type Culture Collection under the accession number ATCC CRL 9595. The AV12 cell line was constructed by injecting a Syrian hamster in the scruff of the neck with human adenovirus 12 and isolating cells from the resulting tumor.

A wide variety of vectors, some of which are discussed below, exists for the transformation of such mammalian host cells, but the specific vectors described herein are in no way intended to limit the scope of the present invention. The sequences encoding the illustrative fusion proteins of the invention are easily removed from the deposited *E. coli* strains by reference to the Figures for selection of the appropriate restriction endonucleases and inserted in any of the vectors described herein through routine purification, ligation and transfection techniques.

The pSV2-type vectors comprise segments of the simian virus 40 (SV40) genome that constitute a defined eukaryotic transcription unit-promoter, intervening sequence, and polyadenylation site. In the absence of the SV40 T antigen, the plasmid pSV2-type vectors transform mammalian and other eukaryotic host cells by integrating into the host cell chromosomal DNA. A large number of plasmid pSV2-type vectors have been constructed, such as plasmid pSV2-gpt, pSV2-neo, pSV2-dhfr, pSV2-hyg, and pSV2-b-globin, in which the SV40 promoter drives transcription of an inserted gene. These vectors are suitable for use with the coding sequences of the present invention and are widely available from sources such as the ATCC or the Northern Regional Research Laboratory (NRRL), 1815 N. University Street, Peoria, Ill., 61604.

The plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification can result in the amplification of closely-associated DNA sequences and can, therefore, be used to increase production of a protein of interest. See, e.g., R. T. Schimke, *Cell*, 35:705–713 (1984).

Plasmids constructed for expression of the proteins of the present invention in mammalian and other eukaryotic host cells can utilize a wide variety of promoters. The present invention is in no way limited to the use of the particular promoters exemplified herein. Promoters such as the SV40 late promoter, promoters from eukaryotic genes, such as, for example, the estrogen-inducible chicken ovalbumin gene, the interferon genes, the gluco-corticoid-inducible tyrosine aminotransferase gene, and the thymidine kinase gene, and the major early and late adenovirus genes can be readily isolated and modified to express the genes of the present invention. Eukaryotic promoters can also be used in tandem to drive expression of a coding sequence of this invention. Furthermore, a large number of retroviruses are known that infect a wide range of eukaryotic host cells. The long terminal repeats in the retroviral DNA frequently encode functional promoters and, therefore, may be used to drive expression of the nucleic acids of the present invention.

Plasmid pRSVcat (ATCC 37152) comprises portions of a long terminal repeat of the Rous Sarcoma virus, a virus known to infect chickens and other host cells. This long terminal repeat contains a promoter which is suitable for use in the vectors of this invention. H. Gorman, et al., *Proceedings of the National Academy of Sciences (USA)*, 79:6777 (1982). The plasmid pMSVi (NRRL B-15929) comprises the long terminal repeats of the Murine Sarcoma virus, a virus known to infect mouse and other host cells. The mouse metallothionein promoter has also been well characterized for use in eukaryotic host cells and is suitable for use in the expression of the nucleic acids of the present invention. The mouse metallothionein promoter is present in the plasmid pdBPV-MMTneo (ATCC 37224) which can serve as the starting material of other plasmids of the present invention.

An especially useful expression vector system employs one of a series of vectors containing the BK enhancer, an enhancer derived from the BK virus, a human papovavirus. The most preferred such vector systems are those which employ not only the BK enhancer but also the adenovirus-2-early region 1A (E1A) gene product. The E1A gene product (actually, the E1A gene produces two products, which are collectively referred to herein as "the E1A gene product") is an immediate-early gene product of adenovirus, a large DNA virus.

A preferred eukaryotic expression vector employed in the present invention is the phd series of vectors which comprise a BK enhancer in tandem with the adenovirus late promoter to drive expression of useful products in eukaryotic host cells. The construction and method of using the phd plasmid, as well as related plasmids, are described in U.S. Pat. No. 5,242,688, issued Sep. 7, 1993, and U.S. Pat. No. 4,992,373, issued Feb. 12, 1991, all of which are herein incorporated by reference. *Escherichia coli* K12 GM48 cells harboring the plasmid phd are available as part of the permanent stock collection of the Northern Regional Research Laboratory under accession number NRRL B-18525. The plasmid may be isolated from this culture using standard techniques.

The plasmid phd contains a unique BclI site which may be utilized for the insertion of the gene encoding the protein of interest. The skilled artisan understands that linkers or adapters may be employed in cloning the gene of interest into this BclI site. The phd series of plasmids functions most efficiently when introduced into a host cell which produces the E1A gene product, cell lines such as AV12-664, 293 cells, and others, described supra.

Transformation of the mammalian cells can be performed by any of the known processes including, but not limited to, the protoplast fusion method, the calcium phosphate co-precipitation method, electroporation and the like. See. e.g., J. Sambrook, et al., supra, at 3:16.30–3:16.66.

Other routes of production are well known to skilled artisans. In addition to the plasmids discussed above, it is well known in the art that some viruses are also appropriate vectors. For example, the adenovirus, the adeno-associated virus, the vaccinia virus, the herpes virus, the baculovirus, and the rous sarcoma virus are useful. Such a method is described in U.S. Pat. No. 4,775,624, herein incorporated by reference. Several alternate methods of expression are described in J. Sambrook, et al., supra, at 16.3–17.44.

In addition to prokaryotes and mammalian host cells, eukaryotic microbes such as yeast cultures may also be used. The imperfect fungus *Saccharomyces cerevisiae*, or common baker's yeast, is the most commonly used eukaryotic microorganism, although a number of other strains are commonly available. For expression in Saccharomyces sp., the plasmid YRp7 (ATCC-40053), for example, is commonly used. See. e.g., L. Stinchcomb, et al., *Nature (London)*, 282:39 (1979); J. Kingsman et al., *Gene*, 7:141 (1979); S. Tschemper et al., *Gene*, 10:157 (1980). This plasmid already contains the trp gene which provides a selectable marker for a mutant strain of yeast lacking the ability to grow in tryptophan.

Suitable promoting sequences for use with yeast hosts include the promoters for 3-phosphoglycerate kinase [found on plasmid pAP12BD (ATCC 53231) and described in U.S. Pat. No. 4,935,350, issued Jun. 19, 1990, herein incorporated by reference] or other glycolytic enzymes such as enolase [found on plasmid pAC1 (ATCC 39532)], glyceraldehyde-3-phosphate dehydrogenase [derived from plasmid pHcGAPC1 (ATCC 57090, 57091)], hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase, as well as the alcohol dehydrogenase and pyruvate decarboxylase genes of *Zymomonas mobilis* (U.S. Pat. No. 5,000,000 issued Mar. 19, 1991, herein incorporated by reference).

Other yeast promoters, which are inducible promoters, having the additional advantage of their transcription being controllable by varying growth conditions, are the promoter regions for alcohol dehydrogenase 2, isocytochrome C, acid phosphatase, degradative enzymes associated with nitrogen metabolism, metallothionein [contained on plasmid vector pCL28XhoLHBPV (ATCC 39475) and described in U.S. Pat. No. 4,840,896, herein incorporated by reference], glyceraldehyde 3-phosphate dehydrogenase, and enzymes responsible for maltose and galactose [e.g. GAL1 found on plasmid pRY121 (ATCC 37658)] utilization. Suitable vectors and promoters for use in yeast expression are further described in R. Hitzeman et al., European Patent Publication No. 73,657A. Yeast enhancers such as the UAS Gal from *Saccharomyces cerevisiae* (found in conjunction with the CYC1 promoter on plasmid YEpsec—hI1beta ATCC 67024), also are advantageously used with yeast promoters.

Skilled artisans also recognize that some alterations of SEQ ID NO:2, 3, 5, 6, 7 or 8 will fail to change the function of the amino acid compound. For instance, some hydrophobic amino acids may be exchanged for other hydrophobic amino acids. Those altered amino acid compounds which confer substantially the same function in substantially the same manner as the exemplified amino acid compound are also encompassed within the present invention. Typically such conservative substitutions attempt to preserve the: (a) secondary or tertiary structure of the polypeptide backbone; (b) the charge or hydrophobicity of the residue; or (c) the bulk of the side chain. Some examples of such conservative substitutions of amino acids, resulting in the production of proteins which are functional equivalents of the proteins of SEQ ID NO:2, 3, 5, 6, 7 or 8 are shown in Table II, infra.

TABLE II

| Original Residue | Exemplary Substitutions |
| --- | --- |
| Ala | Ser, Gly |
| Arg | Lys |
| Asn | Gln, His |
| Asp | Glu |
| Cys | Ser |
| Gln | Asn |
| Glu | Asp |
| Gly | Pro, Ala |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

These substitutions may be introduced into the protein in a variety of ways, such as during the chemical synthesis or by chemical modification of an amino acid side chain after the protein has been prepared.

Alterations of the protein having a sequence which corresponds to the sequences of SEQ ID NO:2, 3, 5, 7 or 8 may also be induced by alterations of the nucleic acid compounds which encodes these proteins. These mutations of the nucleic acid compound may be generated by either random mutagenesis techniques, such as those techniques employing chemical mutagens, or by site-specific mutagenesis employing oligonucleotides. Those nucleic acid compounds which confer substantially the same function in substantially the same manner as the exemplified nucleic acid compounds are also encompassed within the present invention.

Other embodiments of the present invention are nucleic acid compounds which comprise isolated nucleic acid sequences which encode SEQ ID NO: 2, 3, 5, 7, and 8. As skilled artisans will recognize, the amino acid compounds of the invention can be encoded by a multitude of different nucleic acid sequences because most of the amino acids are encoded by more than one nucleic acid triplet due to the degeneracy of the amino acid code. Because these alternative nucleic acid sequences would encode the same amino acid sequences, the present invention further comprises these alternate nucleic acid sequences.

The genes encoding the DNA molecules of the present invention may be produced using synthetic methodology. This synthesis of nucleic acids is well known in the art. See, e.g., E. L. Brown, R. Belagaje, M. J. Ryan, and H. G. Khorana, *Methods in Enzymology,* 68:109–151 (1979). The DNA segments corresponding to the fusion proteins are generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404) which employ phosphoramidite chemistry. In the alternative, the more traditional phosphotriester chemistry may be employed to synthesize the nucleic acids of this invention. See, e.g., M. J. Gait, ed., OLIGONUCLEOTIDE SYNTHESIS, A PRACTICAL APPROACH, (1984).

The DNA sequences of the present invention may be designed to possess restriction endonuclease cleavage sites at either end of the transcript to facilitate isolation from and integration into expression and amplification plasmids. The choice of restriction sites are chosen so as to properly orient the coding sequence with control sequences to achieve proper in-frame reading and expression of the molecule. A variety of other such cleavage sites may be incorporated depending on the particular plasmid constructs employed and may be generated by techniques well known in the art.

In an alternative methodology, the human cyclin and human CDK coding regions of the desired DNA sequences can be generated using the polymerase chain reaction as described in U.S. Pat. No. 4,889,818, which is herein incorporated by reference.

The preferred expression systems for use in the present invention are the various Baculovirus systems. The pFast-Bac1 expression system, which is commercially available from the Life Technologies group of Gibco BRL Products as Catalog No. 10360-016. Life Technologies, P.O. Box 68, Grand Island, N.Y. 14072, Telephone: 800 828 6686, is the preferred expression system when modest amounts of biologically active fusion proteins are desired. The Bac-To-Bac Baculovirus Expression System has been used for expression of the sequences of the present invention and this system is also available from Life Technologies (Catalog No. 10359-016). The present inventors elected to deposit the DNA sequences encoding the illustrative cyclin-CDK fusion proteins as components of prokaryotic, lac operon-regulated expression systems due to the ability of the *E. coli* systems to produce large amounts of the fusion proteins and the ease with which skilled artisans can excise the desired coding sequences from the *E. coli* systems and insert them into these commercially available Baculovirus expression systems to thereby achieve the preferred mode of expressing modest amounts of the illustrative fusion proteins.

Baculovirus expression systems are well known in the art and numerous scientific articles and "methods" books are available on the subject. The present inventors have found the Life Technologies technical literature to provide excellent guidance for producing products of interest via Baculovirus expression. The preferred techniques for Baculovirus expression of the sequences of the present invention are those provided in the product literature. Minor variations such as linker construction and the like are considered in light of the advanced state of this art as too trivial to warrant discussion. In the event skilled artisans elect to depart from the commercially available Baculovirus systems, the present inventors recommend Baculovirus Expression Vectors-A Laboratory Manual, O'Reilly, David R., Miller, Lois K., and Luckow, Verne A., W. H. Freeman and Company, New York, N.Y. as a source of additional information on any protocol required for successful expression of polypeptides in Baculovirus systems.

The assays which are greatly advantaged by the fusion proteins of the present invention are well illustrated in two recent scientific publications: Connell-Crowley, L., et al., Mol. Biol. of the Cell 4, 79–92 (1993) and Desai, D., Mol. Biol. of the Cell 3, 571–582 (1992).

The examples provide sources for reagents, however it will be understood that numerous vendors market reagents of high quality for use in the protocols and procedures described below and the substitution of reagents or protocols is contemplated by the present invention and embraced in the scope thereof. All temperatures unless otherwise noted are expressed in degrees Centigrade. All percentages are on a weight per weight basis unless otherwise noted.

Skilled artisans wishing to practice the recombinant DNA aspects of the present invention are directed to the NIH guidelines for information on research involving recombinant DNA molecules. A copy of the current guidelines can be obtained from Office of Recombinant DNA Activities, National Institutes of Health, Building 31, Room 4B11, Bethesda, Md. 20892. Compliance with all such current regulations regarding vector selection, expression of human and animal genes and containment requirements is required by law.

The examples are intended to further illustrate the present invention and are not to be interpreted as limiting on the scope thereof. While the examples and detailed description sections of the present invention are sufficient to guide anyone of ordinary skill in the art in the practice of the present invention, skilled artisans are also directed to *Molecular Cloning A Laboratory Manual* Second Edition, Sambrook, J., Fritsch, E. F., and Maniatis, T., Cold Spring Harbor Press 1989 and *Current Protocols In Molecular Biology*, Ausubel, F. M., Brent, R., Kingston, R. E., Moore, D. D., Seidman, J. G., Smith, J. A., and Struhl, K., Ed. Greene Publishing Associates and Wiley-Interscience 1989. The aforementioned resources provide an excellent technical supplement to any discourse in genetic engineering.

EXAMPLE 1

Production of Baculovirus System for Expression of SEQ ID NO:2

A sample of NRRL B-21490 is obtained from the NRRL. The sample is cultured according to well known procedures using standard media containing Ampicillin for selection of the desired transformed phenotype.

Plasmid isolation is accomplished in accordance with standard methodology. See e.g. Sambrook and Maniatis, supra.

The desired fragment is excised from plasmid pK415 (See FIG. 1) by sequential digestion with the restriction endonucleases, AscI and Sse 8387I. The AscI digestion is performed using New England Biolabs reagents and protocols. The restriction endonuclease Sse 8387I is available from Takara Biomedicals via PanVera Corp., 565 Science Drive, Madison, Wis. 53711 (1 800 791-1400). The vendors instructions on digestion procedures are recommended.

pFastBac1 is digested with BssHII (New England Biolabs) and PstI (New England Biolabs) in accordance with vendors instructions and the large fragment is isolated. A restriction site and function map of pFastBac1 is provided at page 5 of the GibcoBRL/Life Technologies Catalog Number 10359-016 (Instruction Manual-BAC-TO-BAC™ Baculovirus Expression System). The catalog is herein incorporated by reference. The fusion protein encoding sequence is then ligated into the pFastBac1 vector using standard ligation reagents and conditions. Preferred ligation reagents and conditions are set forth at pages 7 and 8, Section 3.3, of GibcoBRL/Life Technogies Catalog Number 10359-016. Page 5 of GibcoBRL/Life Technogies Catalog Number 10359-016 provides DNA sequence information and restriction endonuclease cleavage sites for the multiple cloning site of pFastBac1 and is therefore useful in the event skilled artisans elect to fragment the sequence from p415 or excise it by other than the restriction endonucleases suggested above and utilize linkers to facilitate the subsequent ligation into pFastBac1.

Transposition of the pFastBac1 vector comprising the fusion protein of plasmid pK415 into DH10Bac10 (competent cells are provided as part of the expression kit accompanying pFastBac1 in Catalog Number 10359-16) is conducted in accordance with the teachings of page 8 of GibcoBRL/Life Technogies Catalog Number 10359-016.

Isolation of Recombinant Bacmid DNA is accomplished in accordance with the teachings of pages 8 and 9 of GibcoBRL/Life Technogies Catalog Number 10359-016.

Transfection of Sf9 cells with recombinant Bacmid DNA, harvesting and storage of the recombinant Baculovirus, and Infection of Insect Cells with recombinant Baculovirus particles is accomplished with the teachings at pages 9 and 10 of GibcoBRL/Life Technogies Catalog Number 10359-016.

EXAMPLE 2

Production of Baculovirus System for Expression of SEQ ID NO:4

Baculovirus expression systems were constructed in substantial accordance with the teachings of Example 1. Plasmid pK480 from *E. coli*/pK485 was used in place of plasmid pk415 as the source of the DNA sequence encoding the fusion protein of interest.

EXAMPLE 3

Production of Baculovirus System for Expression of SEQ ID NO:6

Baculovirus expression systems were constructed in substantial accordance with the teachings of Example 1. Plasmid pK485 from *E. coli*/pK480, NRRL number B21491, was used in place of plasmid pK415 as the source of the DNA sequence encoding the fusion protein of interest. With the exception of the substitution of plasmid pK480 for plasmid pK415 all steps of this Example 3 were carried out in conformance with the teachings of Example 1.

EXAMPLE 4

Purification of Co-expressed D1.K4

Affinity chromatography resins for fusion protein purification are readily constructed from commercially available reagents using techniques well known in the art.

CNBr-activated Sepharose 4B (Pharmacia Fine Chemicals) is the preferred matrix for linkage of appropriate monoclonal or polyclonal antibodies to allow antibody-based affinity purification of the fusion proteins. Pharmacia Fine Chemicals publishes "Affinity Chromatography-Principles and Methods". This manual sets forth all steps in preparing the affinity resin and performing the antibody-based affinity purification steps. The manual is available from Pharmacia Fine Chemicals, Box 175, S-751 04 Uppsala 1, Sweden.

EXAMPLE 5
Strepavadin Purification of Cyclin-CDK Fusion Proteins

The SF9 cells which were utilized in Examples 1–3 as the host cells for Baculovirus expression were collected by centrifugation and resuspended and lysed via sonication at 4° C. in Resuspension Buffer at a density of $8 \times 10^6$/mL. Resuspension buffer is 50 mM HEPES pH 7.5, 0.32M Sucrose, 0.1 mM PMSF, 1.0 mM DTT, 1 mM EDTA and 80 mM β-glycerophosphate.

500 μL of the SF9 extract was added to 200 μL of Streptavidin Paramagnetic Beads (Promega Corporation, 2800 Woods Hollow Road, Madison, Wis. 53711-5399) and the mixture was incubated at room temperature for 45 minutes. The paramagnetic beads were pelleted at room temperature using a MagneSphere Technology Magnetic separation stand (Promega). The beads were washed three times with 1 mL of 1×PBS/25 mg/ml BSA (or 0.1% Tween 20) at room temperature.

The fusion protein was eluted from the beads in 120 μL of Elution Buffer A for 30 minutes at room temperature. Elution Buffer A is 25 mM HEPES pH 7.5, 0.1 mM PMSF, 1 mM d-Biotin 0.1 mM DTT, 20 mM β-glycerophosphate, 1 mMNaF, 10 mM Sodium Orthovanadate and 10% glycerol.

The purified fusion protein was stored at –70° C. until ready for use.

EXAMPLE 6
Ni-NTA Purification of Cyclin-CDK Fusion Proteins $8 \times 10^6$ SF6 cells/mL (from Examples 1–3) were collected by centrifugation and resuspended and lysed at 4° C. in Resuspension Buffer. 1.0 mL of the insect cell extract was added to 3.0 mL of Ni-NTA agarose (Qiagen Inc., 9259 Eton Avenue, Chatsworth, Calif. 91311), which was previously equilibrated with Wash Buffer. Wash Buffer is 50 mM HEPES pH 7.5, 300 mM NaCl, 20 mM Imidizole and 0.1 mM PMSF.

The extract agarose mixture was incubated at 4° C. for 4 hours. The mixture was gently agitated during the incubation. The agarose was then pelleted by centrifugation at 2000×g for two minutes and then washed three times with 5.0 mL of 1×PBS at 4° C. with agitation The fusion protein was eluted from the agarose in 750 μL of Elution Buffer B for 1 hour at 4° C. with agitation. Elution Buffer B is 50 mM HEPES pH 7.5, 300 mM NaCl, 250 mM Imidizole, 0.1 mM PMSF, 10 mM Sodium Orthovanadate, 1 mM NaF and 20 mM β-glycerophosphate. The eluted fusion protein was dialyzed in 3.0 L of Dialysis Buffer overnight at 4° C. Dialysis Buffer is 25 mM HEPES ph 7.5, 10% glycerol, 0.01% Triton-X, 0.1 mM PMSF, 20 mM β-glycerophosphate, 1 mM NaF and 10 mM Sodium Orthovanadate.

The dialyzed fusion protein was stored at –70° C.

EXAMPLE 7
Purification of Co-expressed D1.K4 Individual Units

Purification of co-expressed cyclin D1 and cdk4 was performed at Spinx Pharmaceuticals. Insect cell pellets were homogenized at 1:10 in 50 mM HEPES pH 7.5, 320 mM Sucrose, 1 mM DTT, 0.1 mM PMSF, 1 mM EGTA, 1mM EDTA and 20 μg/ml leupeptin. The lysed cells were spun for 1.5 hrs. at 100,000 xg to remove cytosol then equilibrated a Poros Q column in Equilibration Buffer (25 mM Tris pH 8.0, 10% glycerol, 1 mM DTT, 0.1 mM PMSF, 1 mM EDTA, and 20 μg/ml leupeptin). The lysates were loaded onto a Poros Q column at 5 ml/L of infected insect cells. The Poros Q column was washed with 10-column volumes of Equilibration buffer. The column was eluted with 0–1M NaCl gradient collecting 2 ml/fraction. The column fractions were assayed for activity and peak fractions were pooled. The resulting pool was diluted to give a final NaCl concentration of 100 mM. The dilute pool fractions were loaded onto a Hydroxapatite column equilibrated with 25 mM Tris pH 8.0, 0.1 mM PMSF, 1 mM EDTA, and 20 μg/ml leupeptin. The Hydroxapatite column was washed with 10-column volumes of Equilibration buffer and eluted cyclin D1 and cdk4 with 0–400 mM potassium phosphate, pH 7.5. Column fractions were assayed for activity and the peak fractions pooled. The eluted protein was stored at –70C.

EXAMPLE 8
Immunoprecipitation of D1.K4 Fusion $5 \times 10^6$ cells/mL were lysed in IP Lysis Buffer on ice for 30 minutes (IP Lysis Buffer: 50 mM HEPES pH 7.4, 150 mM NaCl, 1 mM EDTA, 1 mM DTT, 2.5 mM EGTA, 0.1% Tween 20, 10% Glycerol, 0.1 mM PMSF, 500 μM ATP, 10 mM β-glycerophosphate, 1 mM NaF, and 0.1 mM orthovanadate) The cells were sonicated three times on ice for 10 seconds each time, and the lysates were clarified for 5 minutes at 10,000 rpm and 4° C. 20 μL of myc antibody (100 μg/mL commercially available from Oncogene Science, Cambridge, Mass.) was added to 500 μL of clarified cell lysate. The mixture was incubated with agitation for 3 hours at 4° C. 50 μl of 50% Protein-G Agarose (Boehringer Mannheim), which had been washed with IP Lysis Buffer, was then added to each sample. The samples were incubated with agitation for 2–5 hours at 4° C. The Protein-G-Agarose was pelleted and washed 4× with IP Lysis Buffer and then 2× with 50 mM HEPES pH 7.4 and 1 mM DTT. The washed Protein-G-Agarose was resuspended in Kinase Reaction Buffer.

EXAMPLE 9
Assays for Clyclin D1 and cdk4

Partially purified co-expressed or fused cyclin D1 and cdk4 were assayed for Rb kinase activity. Co-expressed cyclin D1 and cdk4 were partially purified as described above. Fused cyclin D1-cdk4 was partially purified by streptavidin beads, Ni-NTA agarose, and by immunoprecipitation. In immunoprecipitations, fused cyclin D1-cdk4 expressed in stably transfected Rat Embryo Fibroblasts (E3600NA-FPr-5) were partially purified as described in Matsushime et al., 1994. Kinase reactions with various amounts of partially purified cyclin D1 and cdk4 from insect cells contained: 50 mM HEPES pH 7.5, 10 mM $MgCl_2$, 0.2 μCi [gamma-$^{32}$P]ATP (Amersham, 6,000 Ci/mmol), 0.12 μg pRb (full-length protein from Immuno Pharmaceutics), 0.1 mM sodium orthovanadate, 10 mM β-glycerophophate and 1 mM NaF in a total of 100 μL. Kinase reactions with immunoprecipitated fusion protein on Protein-G-Agarose (Boehringer Mannheim) from the REF cell line were resuspended in 50 μl of Kinase Reaction Buffer (50 mM HEPES pH 7.5, 10 mM $MgCl_2$, 10.0 μCi [gamma-$^{32}$p]ATP (Amersham, 6,000 Ci/mmol), 0.2 μg pRb (full-length protein from Immuno Pharmaceutics), 1 mM DTT, 2.5 mM EGTA, 20 μM ATP, 0.1 mM sodium orthovanadate, 10 mM β-clycerophophate and 1 mM NaF). Reactions were incubated at 30° C. for 30 minutes, boiled for 5 minutes, and half of the reaction was loaded onto a 12.5% SDS-polyacrylamide gel. The gel was transferred to Hybond-ECL nitrocellulose (Amersham) and exposed to Hyperfilm-ECL (Amersham).

EXAMPLE 10
Immunoblots

For protein detection of cyclin D1 and cdk4, nitrocellulose membranes were blocked with 5% dry milk in 1×PBS for 30 to 60 minutes. Membranes were washed 3×, 10 minutes for each wash, in 1×PBS/0.1% Tween 20. The membrane was incubated with primary antibody (cyclin D1 or cdk4) at a 1:2000 dilution in 1×PBS/0.1% Tween 20/1% Milk for 1 hour at room temperature then washed 3× for 10 minutes each in 1×PBS/0.1% Tween 20. The membrane was then incubated with a secondary antibody (horse radish peroxidase conjugated goat anti-mouse or rabbit antibody from Amersham) at a 1:1000 dilution in 1×PBS/0.1% Tween 20/1% Milk for 25 minutes at room temperature. The membrane was washed 6× in PBS/0.1% Tween 20, 2× in 1×PBS, and developed with Amersham ECL detection reagents. The results indicated that the fusion protein had substantially the same amount of activity as the individual subunits.

We claim:

1. A fusion protein comprising human cyclin D1 and human cyclin dependent kinase 4, said fusion protein having kinase activity.

2. The fusion protein of claim 1 that is SEQ ID NO:2.

3. The fusion protein of claim 1 that is SEQ ID NO:3.

4. The fusion protein of claim 1 that is SEQ ID NO:5.

5. The fusion protein of claim 1 that is SEQ ID NO:7.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 4621 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
GACGAAAGGG  CCTCGTGATA  CGCCTATTTT  TATAGGTTAA  TGTCATGATA  ATAATGGTTT      60
CTTAGACGTC  AGGTGGCACT  TTTCGGGGAA  ATGTGCGCGG  AACCCCTATT  TGTTTATTTT     120
TCTAAATACA  TTCAAATATG  TATCCGCTCA  TGAGACAATA  ACCCTGATAA  ATGCTTCAAT     180
AATATTGAAA  AAGGAAGAGT  ATGAGTATTC  AACATTTCCG  TGTCGCCCTT  ATTCCCTTTT     240
TTGCGGCATT  TTGCCTTCCT  GTTTTTGCTC  ACCCAGAAAC  GCTGGTGAAA  GTAAAAGATG     300
CTGAAGATCA  GTTGGGTGCA  CGAGTGGGTT  ACATCGAACT  GGATCTCAAC  AGCGGTAAGA     360
TCCTTGAGAG  TTTTCGCCCC  GAAGAACGTT  TTCCAATGAT  GAGCACTTTT  AAAGTTCTGC     420
TATGTGGCGC  GGTATTATCC  CGTATTGACG  CCGGGCAAGA  GCAACTCGGT  CGCCGCATAC     480
ACTATTCTCA  GAATGACTTG  GTTGAGTACT  CACCAGTCAC  AGAAAAGCAT  CTTACGGATG     540
GCATGACAGT  AAGAGAATTA  TGCAGTGCTG  CCATAACCAT  GAGTGATAAC  ACTGCGGCCA     600
ACTTACTTCT  GACAACGATC  GGAGGACCGA  AGGAGCTAAC  CGCTTTTTTG  CACAACATGG     660
GGGATCATGT  AACTCGCCTT  GATCGTTGGG  AACCGGAGCT  GAATGAAGCC  ATACCAAACG     720
ACGAGCGTGA  CACCACGATG  CCTGTAGCAA  TGGCAACAAC  GTTGCGCAAA  CTATTAACTG     780
GCGAACTACT  TACTCTAGCT  TCCCGGCAAC  AATTAATAGA  CTGGATGGAG  GCGGATAAAG     840
TTGCAGGACC  ACTTCTGCGC  TCGGCCCTTC  CGGCTGGCTG  GTTTATTGCT  GATAAATCTG     900
GAGCCGGTGA  GCGTGGGTCT  CGCGGTATCA  TTGCAGCACT  GGGGCCAGAT  GGTAAGCCCT     960
CCCGTATCGT  AGTTATCTAC  ACGACGGGGA  GTCAGGCAAC  TATGGATGAA  CGAAATAGAC    1020
AGATCGCTGA  GATAGGTGCC  TCACTGATTA  AGCATTGGTA  ACTGTCAGAC  CAAGTTTACT    1080
CATATATACT  TTAGATTGAT  TTAAAACTTC  ATTTTTAATT  TAAAAGGATC  TAGGTGAAGA    1140
TCCTTTTTGA  TAATCTCATG  ACCAAAATCC  CTTAACGTGA  GTTTTCGTTC  CACTGAGCGT    1200
CAGACCCCGT  AGAAAAGATC  AAAGGATCTT  CTTGAGATCC  TTTTTTTCTG  CGCGTAATCT    1260
GCTGCTTGCA  AACAAAAAAA  CCACCGCTAC  CAGCGGTGGT  TGTTTGCCGG  ATCAAGAGCT    1320
ACCAACTCTT  TTTCCGAAGG  TAACTGGCTT  CAGCAGAGCG  CAGATACCAA  ATACTGTCCT    1380
TCTAGTGTAG  CCGTAGTTAG  GCCACCACTT  CAAGAACTCT  GTAGCACCGC  CTACATACCT    1440
CGCTCTGCTA  ATCCTGTTAC  CAGTGGCTGC  TGCCAGTGGC  GATAAGTCGT  GTCTTACCGG    1500
```

```
GTTGGACTCA AGACGATAGT TACCGGATAA GGCGCAGCGG TCGGGCTGAA CGGGGGGTTC     1560
GTGCACACAG CCCAGCTTGG AGCGAACGAC CTACACCGAA CTGAGATACC TACAGCGTGA     1620
GCATTGAGAA AGCGCCACGC TTCCCGAAGG GAGAAAGGCG GACAGGTATC CGGTAAGCGG     1680
CAGGGTCGGA ACAGGAGAGC GCACGAGGGA GCTTCCAGGG GGAAACGCCT GGTATCTTTA     1740
TAGTCCTGTC GGGTTTCGCC ACCTCTGACT TGAGCGTCGA TTTTTGTGAT GCTCGTCAGG     1800
GGGGCGGAGC CTATGGAAAA ACGCCAGCAA CGCGGCCTTT TTACGGTTCC TGGCCTTTTG     1860
CTGGCCTTTT GCTCACATGT TCTTTCCTGC GTTATCCCCT GATTCTGTGG ATAACCGTAT     1920
TACCGCCTTT GAGTGAGCTG ATACCGCTCG CCGCAGCCGA ACGACCGAGC GCAGCGAGTC     1980
AGTGAGCGAG GAAGCGGAAG AGCGCCCAAT ACGCAAACCG CCTCTCCCCG CGCGTTGGCC     2040
GATTCATTAA TGCAGCTGGC ACGACAGGTT TCCCGACTGG AAAGCGGGCA GTGAGCGCAA     2100
CGCAATTAAT GTGAGTTAGC TCACTCATTA GGCACCCCAG GCTTTACACT TTATGCTTCC     2160
GGCTCGTATG TTGTGTGGAA TTGTGAGCGG ATAACAATTT CACACAGGAA ACAGCTATGA     2220
CCATGATTAC GCCAAGCTTA CGGCGCGCCG CCGCCACCAT GGCGGAGGAG CAGAAGCTGA     2280
TATCCGAGGA GGACCTGCTG CTAGCAATGG AACACCAGCT CCTGTGCTGC GAAGTGGAAA     2340
CCATCCGCCG CGCGTACCCC GATGCCAACC TCCTCAACGA CCGGGTGCTG CGGGCCATGC     2400
TGAAGGCGGA GGAGACCTGC GCGCCCTCGG TGTCCTACTT CAAATGTGTG CAAAAGGAGG     2460
TCCTGCCGTC CATGCGGAAG ATCGTCGCCA CCTGGATGCT GGAGGTCTGC GAGGAACAGA     2520
AGTGCGAGGA GGAGGTCTTC CCGCTGGCCA TGAACTACCT GGACCGCTTC CTGTCGCTGG     2580
AGCCCGTGAA AAAGAGCCGC CTGCAGCTGC TGGGGGCCAC TTGCATGTTC GTGGCCTCTA     2640
AGATGAAGGA GACCATCCCC CTGACGGCCG AGAAGCTGTG CATCTACACC GACAACTCCA     2700
TCCGGCCCGA GGAGCTGCTG CAAATGGAGC TGCTCCTGGT GAACAAGCTC AAGTGGAACC     2760
TGGCCGCAAT GACCCCGCAC GATTTCATTG AACACTTCCT CTCCAAAATG CCAGAGGCGG     2820
AGGAGAACAA ACAGATCATC CGCAAACACG CGCAGACCTT CGTTGCCCTC TGTGCCACAG     2880
ATGTGAAGTT CATTTCCAAT CCGCCCTCCA TGGTGGCAGC GGGGAGCGTG GTGGCCGCAG     2940
TGCAAGGCCT GAACCTGAGG AGCCCCAACA ACTTCCTGTC CTACTACCGC CTCACACGCT     3000
TCCTCTCCAG AGTGATCAAG TGTGACCCAG ACTGCCTCCG GGCCTGCCAG GAGCAGATCG     3060
AAGCCCTGCT GGAGTCAAGC CTGCGCCAGG CCCAGCAGAA CATGGACCCC AAGGCCGCCG     3120
AGGAGGAGGA GGAGGAAGAG GAGGAAGAGG AGGTGGACCT GGCTTGCACA CCCACCGACG     3180
TGCGGGACGT GGACATCGCA TCGAAGGGTG GTGGAGGTTC TGGAGGTGGA GGATCCGGTG     3240
GTGGAGGTTC GATGGCTACC TCTCGATATG AGCCAGTGGC TGAAATTGGT GTCGGTGCCT     3300
ATGGGACAGT GTACAAGGCC CGTGATCCCC ACAGTGGCCA CTTTGTGGCC CTCAAGAGTG     3360
TGAGAGTCCC CAATGGAGGA GGAGGTGGAG GAGGCCTTCC CATCAGCACA GTTCGTGAGG     3420
TGGCTTTACT GAGGCGACTG GAGGCTTTTG AGCATCCCAA TGTTGTCCGG CTGATGGACG     3480
TCTGTGCCAC ATCCCGAACT GACCGGGAGA TCAAGGTAAC CCTGGTGTTT GAGCATGTAG     3540
ACCAGGACCT AAGGACATAT CTGGACAAGG CACCCCCACC AGGCTTGCCA GCCGAAACGA     3600
TCAAGGATCT GATGCGCCAG TTTCTAAGAG GCCTAGATTT CCTTCATGCC AATTGCATCG     3660
TTCACCGAGA TCTGAAGCCA GAGAACATTC TGGTGACAAG TGGTGGAACA GTCAAGCTGG     3720
CTGACTTTGG CCTGGCCAGA ATCTACAGCT ACCAGATGGC ACTTACACCC GTGGTTGTTA     3780
CACTCTGGTA CCGAGCTCCC GAAGTTCTTC TGCAGTCCAC ATATGCAACA CCTGTGGACA     3840
TGTGGAGTGT TGGCTGTATC TTTGCAGAGA TGTTTCGTCG AAAGCCTCTC TTCTGTGGAA     3900
```

```
ACTCTGAAGC CGACCAGTTG GGCAAAATCT TTGACCTGAT TGGGCTGCCT CCAGAGGATG      3960

ACTGGCCTCG AGATGTATCC CTGCCCCGTG GAGCCTTTCC CCCCAGAGGG CCCCGCCCAG      4020

TGCAGTCGGT GGTACCTGAG ATGGAGGAGT CGGGAGCACA GCTGCTGCTG GAAATGCTGA      4080

CTTTTAACCC ACACAAGCGA ATCTCTGCCT TTCGAGCTCT GCAGCACTCT TATCTACATA      4140

AGGATGAAGG TAATCCGGAG GGCGGCAGCG CTTGGCGCCA CCCACAGTTC GGTGGTTGAA      4200

TAAATAGATG AATGACCTGC AGGTTCACTG GCCGTCGTTT TACAACGTCG TGACTGGGAA      4260

AACCCTGGCG TTACCCAACT TAATCGCCTT GCAGCACATC CCCCTTTCGC CAGCTGGCGT      4320

AATAGCGAAG AGGCCCGCAC CGATCGCCCT TCCCAACAGT TGCGCAGCCT GAATGGCGAA      4380

TGGCGCCTGA TGCGGTATTT TCTCCTTACG CATCTGTGCG GTATTTCACA CCGCATATGG      4440

TGCACTCTCA GTACAATCTG CTCTGATGCC GCATAGTTAA GCCAGCCCCG ACACCCGCCA      4500

ACACCCGCTG ACGCGCCCTG ACGGGCTTGT CTGCTCCCGG CATCCGCTTA CAGACAAGCT      4560

GTGACCGTCT CCGGGAGCTG CATGTGTCAG AGGTTTTCAC CGTCATCACC GAAACGCGCG      4620

A                                                                     4621
```

(2) INFORMATION FOR SEQ ID NO:2:

(i) SEQUENCE CHARACTERISTICS:
        (A) LENGTH: 660 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met Thr Met Ile Thr Pro Ser Leu Arg Arg Ala Ala Ala Thr Met Ala
 1               5                  10                  15

Glu Glu Gln Lys Leu Ile Ser Glu Glu Asp Leu Leu Leu Ala Met Glu
                20                  25                  30

His Gln Leu Leu Cys Cys Glu Val Glu Thr Ile Arg Arg Ala Tyr Pro
            35                  40                  45

Asp Ala Asn Leu Leu Asn Asp Arg Val Leu Arg Ala Met Leu Lys Ala
        50                  55                  60

Glu Thr Cys Ala Pro Ser Val Ser Tyr Phe Lys Cys Val Gln Lys
 65                  70                  75                  80

Glu Val Leu Pro Ser Met Arg Lys Ile Val Ala Thr Trp Met Leu Glu
                85                  90                  95

Val Cys Glu Glu Gln Lys Cys Glu Glu Glu Val Phe Pro Leu Ala Met
                100                 105                 110

Asn Tyr Leu Asp Arg Phe Leu Ser Leu Glu Pro Val Lys Lys Ser Arg
            115                 120                 125

Leu Gln Leu Leu Gly Ala Thr Cys Met Phe Val Ala Ser Lys Met Lys
        130                 135                 140

Glu Thr Ile Pro Leu Thr Ala Glu Lys Leu Cys Ile Tyr Thr Asp Asn
145                 150                 155                 160

Ser Ile Arg Pro Glu Glu Leu Leu Gln Met Glu Leu Leu Leu Val Asn
                165                 170                 175

Lys Leu Lys Trp Asn Leu Ala Ala Met Thr Pro His Asp Phe Ile Glu
            180                 185                 190

His Phe Leu Ser Lys Met Pro Glu Ala Glu Glu Asn Lys Gln Ile Ile
        195                 200                 205

Arg Lys His Ala Gln Thr Phe Val Ala Leu Cys Ala Thr Asp Val Lys
```

```
            210                       215                       220
Phe  Ile  Ser  Asn  Pro  Ser  Met  Val  Ala  Ala  Gly  Ser  Val  Val  Ala
225                 230                      235                           240

Ala  Val  Gln  Gly  Leu  Asn  Leu  Arg  Ser  Pro  Asn  Asn  Phe  Leu  Ser  Tyr
                    245                      250                          255

Tyr  Arg  Leu  Thr  Arg  Phe  Leu  Ser  Arg  Val  Ile  Lys  Cys  Asp  Pro  Asp
                    260                      265                 270

Cys  Leu  Arg  Ala  Cys  Gln  Glu  Gln  Ile  Glu  Ala  Leu  Leu  Glu  Ser  Ser
               275                 280                     285

Leu  Arg  Gln  Ala  Gln  Gln  Asn  Met  Asp  Pro  Lys  Ala  Ala  Glu  Glu  Glu
          290                 295                     300

Glu  Glu  Glu  Glu  Glu  Glu  Glu  Val  Asp  Leu  Ala  Cys  Thr  Pro  Thr
305                      310                     315                          320

Asp  Val  Arg  Asp  Val  Asp  Ile  Ala  Ser  Lys  Gly  Gly  Gly  Gly  Ser  Gly
                    325                      330                          335

Gly  Gly  Gly  Ser  Gly  Gly  Gly  Gly  Ser  Met  Ala  Thr  Ser  Arg  Tyr  Glu
               340                      345                         350

Pro  Val  Ala  Glu  Ile  Gly  Val  Gly  Ala  Tyr  Gly  Thr  Val  Tyr  Lys  Ala
               355                      360                     365

Arg  Asp  Pro  His  Ser  Gly  His  Phe  Val  Ala  Leu  Lys  Ser  Val  Arg  Val
          370                 375                     380

Pro  Asn  Gly  Gly  Gly  Gly  Gly  Gly  Gly  Leu  Pro  Ile  Ser  Thr  Val  Arg
385                      390                     395                          400

Glu  Val  Ala  Leu  Leu  Arg  Arg  Leu  Glu  Ala  Phe  Glu  His  Pro  Asn  Val
                    405                      410                          415

Val  Arg  Leu  Met  Asp  Val  Cys  Ala  Thr  Ser  Arg  Thr  Asp  Arg  Glu  Ile
               420                 425                     430

Lys  Val  Thr  Leu  Val  Phe  Glu  His  Val  Asp  Gln  Asp  Leu  Arg  Thr  Tyr
          435                 440                     445

Leu  Asp  Lys  Ala  Pro  Pro  Pro  Gly  Leu  Pro  Ala  Glu  Thr  Ile  Lys  Asp
     450                 455                     460

Leu  Met  Arg  Gln  Phe  Leu  Arg  Gly  Leu  Asp  Phe  Leu  His  Ala  Asn  Cys
465                      470                     475                          480

Ile  Val  His  Arg  Asp  Leu  Lys  Pro  Glu  Asn  Ile  Leu  Val  Thr  Ser  Gly
               485                      490                          495

Gly  Thr  Val  Lys  Leu  Ala  Asp  Phe  Gly  Leu  Ala  Arg  Ile  Tyr  Ser  Tyr
               500                      505                         510

Gln  Met  Ala  Leu  Thr  Pro  Val  Val  Thr  Leu  Trp  Tyr  Arg  Ala  Pro
          515                 520                     525

Glu  Val  Leu  Leu  Gln  Ser  Thr  Tyr  Ala  Thr  Pro  Val  Asp  Met  Trp  Ser
     530                 535                     540

Val  Gly  Cys  Ile  Phe  Ala  Glu  Met  Phe  Arg  Arg  Lys  Pro  Leu  Phe  Cys
545                      550                     555                          560

Gly  Asn  Ser  Glu  Ala  Asp  Gln  Leu  Gly  Lys  Ile  Phe  Asp  Leu  Ile  Gly
                    565                      570                          575

Leu  Pro  Pro  Glu  Asp  Asp  Trp  Pro  Arg  Asp  Val  Ser  Leu  Pro  Arg  Gly
               580                      585                          590

Ala  Phe  Pro  Pro  Arg  Gly  Pro  Arg  Pro  Val  Gln  Ser  Val  Val  Pro  Glu
          595                      600                     605

Met  Glu  Glu  Ser  Gly  Ala  Gln  Leu  Leu  Leu  Glu  Met  Leu  Thr  Phe  Asn
     610                      615                     620

Pro  His  Lys  Arg  Ile  Ser  Ala  Phe  Arg  Ala  Leu  Gln  His  Ser  Tyr  Leu
625                      630                     635                          640
```

His Lys Asp Glu Gly Asn Pro Glu Gly Gly Ser Ala Trp Arg His Pro
              645                 650                 655

Gln Phe Gly Gly
            660

(2) INFORMATION FOR SEQ ID NO:3:

(i) SEQUENCE CHARACTERISTICS:
        (A) LENGTH: 618 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Met Glu His Gln Leu Leu Cys Cys Glu Val Glu Thr Ile Arg Arg Ala
 1               5                  10                  15

Tyr Pro Asp Ala Asn Leu Leu Asn Asp Arg Val Leu Arg Ala Met Leu
             20                  25                  30

Lys Ala Glu Glu Thr Cys Ala Pro Ser Val Ser Tyr Phe Lys Cys Val
             35                  40                  45

Gln Lys Glu Val Leu Pro Ser Met Arg Lys Ile Val Ala Thr Trp Met
 50                  55                  60

Leu Glu Val Cys Glu Glu Gln Lys Cys Glu Glu Val Phe Pro Leu
 65                  70                  75                  80

Ala Met Asn Tyr Leu Asp Arg Phe Leu Ser Leu Glu Pro Val Lys Lys
                 85                  90                  95

Ser Arg Leu Gln Leu Leu Gly Ala Thr Cys Met Phe Val Ala Ser Lys
                 100                 105                 110

Met Lys Glu Thr Ile Pro Leu Thr Ala Glu Lys Leu Cys Ile Tyr Thr
             115                 120                 125

Asp Asn Ser Ile Arg Pro Glu Glu Leu Leu Gln Met Glu Leu Leu Leu
 130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Glu Asn Lys Gln
                 165                 170                 175

Ile Ile Arg Lys His Ala Gln Thr Phe Val Ala Leu Cys Ala Thr Asp
             180                 185                 190

Val Lys Phe Ile Ser Asn Pro Pro Ser Met Val Ala Ala Gly Ser Val
             195                 200                 205

Val Ala Ala Val Gln Gly Leu Asn Leu Arg Ser Pro Asn Asn Phe Leu
210                 215                 220

Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
             245                 250                 255

Ser Ser Leu Arg Gln Ala Gln Gln Asn Met Asp Pro Lys Ala Ala Glu
             260                 265                 270

Glu Glu Glu Glu Glu Glu Glu Glu Glu Glu Val Asp Leu Ala Cys Thr
             275                 280                 285

Pro Thr Asp Val Arg Asp Val Asp Ile Ala Ser Lys Gly Gly Gly Gly
             290                 295                 300

Ser Gly Gly Gly Gly Ser Gly Gly Gly Gly Ser Met Ala Thr Ser Arg
305                 310                 315                 320

Tyr Glu Pro Val Ala Glu Ile Gly Val Gly Ala Tyr Gly Thr Val Tyr 325                                        330                                        335
           Lys   Ala   Arg   Asp   Pro   His   Ser   Gly   His   Phe   Val   Ala   Leu   Lys   Ser   Val
                             340                          345                          350
           Arg   Val   Pro   Asn   Gly   Gly   Gly   Gly   Gly   Gly   Leu   Pro   Ile   Ser   Thr
                             355                          360                          365
           Val   Arg   Glu   Val   Ala   Leu   Leu   Arg   Arg   Leu   Glu   Ala   Phe   Glu   His   Pro
                 370                          375                          380
           Asn   Val   Val   Arg   Leu   Met   Asp   Val   Cys   Ala   Thr   Ser   Arg   Thr   Asp   Arg
           385                          390                          395                          400
           Glu   Ile   Lys   Val   Thr   Leu   Val   Phe   Glu   His   Val   Asp   Gln   Asp   Leu   Arg
                                   405                          410                          415
           Thr   Tyr   Leu   Asp   Lys   Ala   Pro   Pro   Pro   Gly   Leu   Pro   Ala   Glu   Thr   Ile
                             420                          425                          430
           Lys   Asp   Leu   Met   Arg   Gln   Phe   Leu   Arg   Gly   Leu   Asp   Phe   Leu   His   Ala
                             435                          440                          445
           Asn   Cys   Ile   Val   His   Arg   Asp   Leu   Lys   Pro   Glu   Asn   Ile   Leu   Val   Thr
                 450                          455                          460
           Ser   Gly   Gly   Thr   Val   Lys   Leu   Ala   Asp   Phe   Gly   Leu   Ala   Arg   Ile   Tyr
           465                          470                          475                          480
           Ser   Tyr   Gln   Met   Ala   Leu   Thr   Pro   Val   Val   Val   Thr   Leu   Trp   Tyr   Arg
                             485                          490                          495
           Ala   Pro   Glu   Val   Leu   Leu   Gln   Ser   Thr   Tyr   Ala   Thr   Pro   Val   Asp   Met
                             500                          505                          510
           Trp   Ser   Val   Gly   Cys   Ile   Phe   Ala   Glu   Met   Phe   Arg   Arg   Lys   Pro   Leu
                             515                          520                          525
           Phe   Cys   Gly   Asn   Ser   Glu   Ala   Asp   Gln   Leu   Gly   Lys   Ile   Phe   Asp   Leu
                             530                          535                          540
           Ile   Gly   Leu   Pro   Pro   Glu   Asp   Asp   Trp   Pro   Arg   Asp   Val   Ser   Leu   Pro
           545                          550                          555                          560
           Arg   Gly   Ala   Phe   Pro   Pro   Arg   Gly   Pro   Arg   Pro   Val   Gln   Ser   Val   Val
                             565                          570                          575
           Pro   Glu   Met   Glu   Glu   Ser   Gly   Ala   Gln   Leu   Leu   Leu   Glu   Met   Leu   Thr
                             580                          585                          590
           Phe   Asn   Pro   His   Lys   Arg   Ile   Ser   Ala   Phe   Arg   Ala   Leu   Gln   His   Ser
                             595                          600                          605
           Tyr   Leu   His   Lys   Asp   Glu   Gly   Asn   Pro   Glu
                 610                          615

( 2 ) INFORMATION FOR SEQ ID NO:4:

( i ) SEQUENCE CHARACTERISTICS:
        ( A ) LENGTH: 4453 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GACGAAAGGG CCTCGTGATA CGCCTATTTT TATAGGTTAA TGTCATGATA ATAATGGTTT            60

CTTAGACGTC AGGTGGCACT TTTCGGGGAA ATGTGCGCGG AACCCCTATT TGTTTATTTT          120

TCTAAATACA TTCAAATATG TATCCGCTCA TGAGACAATA ACCCTGATAA ATGCTTCAAT          180

AATATTGAAA AAGGAAGAGT ATGAGTATTC AACATTTCCG TGTCGCCCTT ATTCCCTTTT          240

TTGCGGCATT TTGCCTTCCT GTTTTTGCTC ACCCAGAAAC GCTGGTGAAA GTAAAAGATG          300

CTGAAGATCA GTTGGGTGCA CGAGTGGGTT ACATCGAACT GGATCTCAAC AGCGGTAAGA          360

```
TCCTTGAGAG TTTTCGCCCC GAAGAACGTT TTCCAATGAT GAGCACTTTT AAAGTTCTGC      420
TATGTGGCGC GGTATTATCC CGTATTGACG CCGGGCAAGA GCAACTCGGT CGCCGCATAC      480
ACTATTCTCA GAATGACTTG GTTGAGTACT CACCAGTCAC AGAAAAGCAT CTTACGGATG      540
GCATGACAGT AAGAGAATTA TGCAGTGCTG CCATAACCAT GAGTGATAAC ACTGCGGCCA      600
ACTTACTTCT GACAACGATC GGAGGACCGA AGGAGCTAAC CGCTTTTTG CACAACATGG       660
GGGATCATGT AACTCGCCTT GATCGTTGGG AACCGGAGCT GAATGAAGCC ATACCAAACG      720
ACGAGCGTGA CACCACGATG CCTGTAGCAA TGGCAACAAC GTTGCGCAAA CTATTAACTG      780
GCGAACTACT TACTCTAGCT TCCCGGCAAC AATTAATAGA CTGGATGGAG GCGGATAAAG      840
TTGCAGGACC ACTTCTGCGC TCGGCCCTTC CGGCTGGCTG GTTATTGCT GATAAATCTG       900
GAGCCGGTGA GCGTGGGTCT CGCGGTATCA TTGCAGCACT GGGGCCAGAT GGTAAGCCCT      960
CCCGTATCGT AGTTATCTAC ACGACGGGGA GTCAGGCAAC TATGGATGAA CGAAATAGAC     1020
AGATCGCTGA GATAGGTGCC TCACTGATTA AGCATTGGTA ACTGTCAGAC CAAGTTTACT     1080
CATATATACT TTAGATTGAT TTAAAACTTC ATTTTAATT TAAAGGATC TAGGTGAAGA       1140
TCCTTTTTGA TAATCTCATG ACCAAAATCC CTTAACGTGA GTTTTCGTTC CACTGAGCGT     1200
CAGACCCCGT AGAAAAGATC AAAGGATCTT CTTGAGATCC TTTTTTTCTG CGCGTAATCT     1260
GCTGCTTGCA ACAAAAAAA CCACCGCTAC CAGCGGTGGT TTGTTTGCCG GATCAAGAGC      1320
TACCAACTCT TTTTCCGAAG GTAACTGGCT TCAGCAGAGC GCAGATACCA AATACTGTCC     1380
TTCTAGTGTA GCCGTAGTTA GGCCACCACT TCAAGAACTC TGTAGCACCG CCTACATACC     1440
TCGCTCTGCT AATCCTGTTA CCAGTGGCTG CTGCCAGTGG CGATAAGTCG TGTCTTACCG     1500
GGTTGGACTC AAGACGATAG TTACCGGATA AGGCGCAGCG GTCGGGCTGA ACGGGGGGTT     1560
CGTGCACACA GCCCAGCTTG GAGCGAACGA CCTACACCGA ACTGAGATAC CTACAGCGTG     1620
AGCATTGAGA AAGCGCCACG CTTCCCGAAG GGAGAAAGGC GGACAGGTAT CCGGTAAGCG     1680
GCAGGGTCGG AACAGGAGAG CGCACGAGGG AGCTTCCAGG GGGAAACGCC TGGTATCTTT     1740
ATAGTCCTGT CGGGTTTCGC CACCTCTGAC TTGAGCGTCG ATTTTTGTGA TGCTCGTCAG     1800
GGGGGCGGAG CCTATGGAAA AACGCCAGCA ACGCGGCCTT TTTACGGTTC CTGGCCTTTT     1860
GCTGGCCTTT TGCTCACATG TTCTTTCCTG CGTTATCCCC TGATTCTGTG ATAACCGTA     1920
TTACCGCCTT TGAGTGAGCT GATACCGCTC GCCGCAGCCG AACGACCGAG CGCAGCGAGT     1980
CAGTGAGCGA GGAAGCGGAA GAGCGCCCAA TACGCAAACC GCCTCTCCCC GCGCGTTGGC     2040
CGATTCATTA ATGCAGCTGG CACGACAGGT TTCCCGACTG GAAAGCGGGC AGTGAGCGCA     2100
ACGCAATTAA TGTGAGTTAG CTCACTCATT AGGCACCCCA GGCTTTACAC TTTATGCTTC     2160
CGGCTCGTAT GTTGTGTGGA ATTGTGAGCG GATAACAATT TCACACAGGA AACAGCTATG     2220
ACCATGATTA CGCCAAGCTT ACGGCGCGCC GCCGCCACCA TGGCGCATCA TCATCATCAT     2280
CATGGAGGTG GAGGTTCGGA GCAGAAGCTT ATTTCCGAGG AGGATCTGCT GGTGCCACGC     2340
GGTTCCCTGC TAGCAATGGA ACACCAGCTC CTGTGCTGCG AAGTGGAAAC CATCCGCCGC     2400
GCGTACCCCG ATGCCAACCT CCTCAACGAC CGGGTGCTGC GGGCCATGCT AAAGGCGGAG     2460
GAGACCTGCG CGCCCTCGGT GTCCTACTTC AAATGTGTGC AAAAGGAGGT CCTGCCGTCC     2520
ATGCGGAAGA TCGTCGCCAC CTGGATGCTG GAGGTCTGCG AGGAACAGAA GTGCGAGGAG     2580
GAGGTCTTCC CGCTGGCCAT GAACTACCTG GACCGCTTCC TGTCGCTGGA GCCCGTGAAA     2640
AAGAGCCGCC TGCAGCTGCT GGGGGCCACT TGCATGTTCG TGGCCTCTAA GATGAAGGAG     2700
ACCATCCCCC TGACGGCCGA GAAGCTGTGC ATCTACACCG ACAACTCCAT CCGGCCCGAG     2760
```

-continued

```
GAGCTGCTGC AAATGGAGCT GCTCCTGGTG AACAAGCTCA AGTGGAACCT GGCCGCAATG    2820
ACCCCGCACG ATTTCATTGA ACACTTCCTC TCCAAAATGC AGAGGCGGA GGAGAACAAA     2880
CAGATCATCC GCAAACACGC GCAGACCTTC GTTGCCCTCT GTGCCACAGA TGTGAAGTTC    2940
ATTTCCAATC CGCCCTCCAT GGTGGCAGCG GGGAGCGTGG TGGCCGCAGT GCAAGGCCTG    3000
AACCTGAGGA GCCCCAACAA CTTCCTGTCC TACTACCGCC TCACACGCTT CCTCTCCAGA    3060
GTGATCAAGT GTGACCCAGA CTGCCTCCGG GCCTGCCAGG AGCAGATCGA AGCCCTGCTG    3120
GAGTCAAGCC TGCGCCAGGC CCAGCAGAAC ATGGACCCCA AGGCCGCCGA GGAGGAGGAG    3180
GAGGAAGAGG AGGAAGAGGA GGTGGACCTG GCTTGCACAC CCACCGACGT GCGGGACGTG    3240
GACATCGCAT CGAAGGGTGG TGGAGGTTCT GGAGGTGGAG GATCCGGTGG TGGAGGTTCG    3300
ATGGCTACCT CTCGATATGA GCCAGTGGCT GAAATTGGTG TCGGTGCCTA TGGGACAGTG    3360
TACAAGGCCC GTGATCCCCA CAGTGGCCAC TTTGTGGCCC TCAAGAGTGT GAGAGTCCCC    3420
AATGGAGGAG GAGGTGGAGG AGGCCTTCCC ATCAGCACAG TTCGTGAGGT GGCTTTACTG    3480
AGGCGACTGG AGGCTTTTGA GCATCCCAAT GTTGTCCGGC TGATGGACGT CTGTGCCACA    3540
TCCCGAACTG ACCGGGAGAT CAAGGTAACC CTGGTGTTTG AGCATGTAGA CCAGGACCTA    3600
AGGACATATC TGGACAAGGC ACCCCACCA GGCTTGCCAG CCGAAACGAT CAAGGATCTG     3660
ATGCGCCAGT TTCTAAGAGG CCTAGATTTC CTTCATGCCA ATTGCATCGT TCACCGAGAT    3720
CTGAAGCCAG AGAACATTCT GGTGACAAGT GGTGGAACAG TCAAGCTGGC TGACTTTGGC    3780
CTGGCCAGAA TCTACAGCTA CCAGATGGCA CTTACACCCG TGGTTGTTAC ACTCTGGTAC    3840
CGAGCTCCCG AAGTTCTTCT GCAGTCCACA TATGCAACAC CTGTGGACAT GTGGAGTGTT    3900
GGCTGTATCT TTGCAGAGAT GTTTCGTCGA AAGCCTCTCT TCTGTGGAAA CTCTGAAGCC    3960
GACCAGTTGG GCAAAATCTT TGACCTGATT GGGCTGCCTC CAGAGGATGA CTGGCCTCGA    4020
GATGTATCCC TGCCCCGTGG AGCCTTTCCC CCCAGAGGGC CCGCCCAGT GCAGTCGGTG     4080
GTACCTGAGA TGGAGGAGTC GGGAGCACAG CTGCTGCTGG AAATGCTGAC TTTTAACCCA    4140
CACAAGCGAA TCTCTGCCTT TCGAGCTCTG CAGCACTCTT ATCTACATAA GGATGAAGGT    4200
AATCCGGAGG GCGGCAGCGC TTGGCGCCAC CCACAGTTCG GTGGTTGAAT AAATAGATGA    4260
ATGACCTGCA GGTGCACTCT CAGTACAATC TGCTCTGATG CCGCATAGTT AAGCCAGCCC    4320
CGACACCCGC CAACACCCGC TGACGCGCCC TGACGGGCTT GTCTGCTCCC GGCATCCGCT    4380
TACAGACAAG CTGTGACCGT CTCCGGGAGC TGCATGTGTC AGAGGTTTTC ACCGTCATCA    4440
CCGAAACGCG CGA                                                      4453
```

( 2 ) INFORMATION FOR SEQ ID NO:5:

( i ) SEQUENCE CHARACTERISTICS:
        ( A ) LENGTH: 662 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Met Ala His His His His His His Gly Gly Gly Gly Ser Glu Gln Lys
 1               5                  10                  15

Leu Ile Ser Glu Glu Asp Leu Leu Val Pro Arg Gly Ser Leu Leu Ala
            20                  25                  30

Met Glu His Gln Leu Leu Cys Cys Glu Val Glu Thr Ile Arg Arg Ala
        35                  40                  45
```

```
Tyr Pro Asp Ala Asn Leu Leu Asn Asp Arg Val Leu Arg Ala Met Leu
 50                  55                  60

Lys Ala Glu Glu Thr Cys Ala Pro Ser Val Ser Tyr Phe Lys Cys Val
 65                  70                  75                  80

Gln Lys Glu Val Leu Pro Ser Met Arg Lys Ile Val Ala Thr Trp Met
                 85                  90                  95

Leu Glu Val Cys Glu Glu Gln Lys Cys Glu Glu Val Phe Pro Leu
                100                 105                 110

Ala Met Asn Tyr Leu Asp Arg Phe Leu Ser Leu Glu Pro Val Lys Lys
             115                 120                 125

Ser Arg Leu Gln Leu Leu Gly Ala Thr Cys Met Phe Val Ala Ser Lys
    130                 135                 140

Met Lys Glu Thr Ile Pro Leu Thr Ala Glu Lys Leu Cys Ile Tyr Thr
145                 150                 155                 160

Asp Asn Ser Ile Arg Pro Glu Glu Leu Leu Gln Met Glu Leu Leu Leu
                165                 170                 175

Val Asn Lys Leu Lys Trp Asn Leu Ala Ala Met Thr Pro His Asp Phe
            180                 185                 190

Ile Glu His Phe Leu Ser Lys Met Pro Glu Ala Glu Glu Asn Lys Gln
        195                 200                 205

Ile Ile Arg Lys His Ala Gln Thr Phe Val Ala Leu Cys Ala Thr Asp
210                 215                 220

Val Lys Phe Ile Ser Asn Pro Pro Ser Met Val Ala Ala Gly Ser Val
225                 230                 235                 240

Val Ala Ala Val Gln Gly Leu Asn Leu Arg Ser Pro Asn Asn Phe Leu
                245                 250                 255

Ser Tyr Tyr Arg Leu Thr Arg Phe Leu Ser Arg Val Ile Lys Cys Asp
            260                 265                 270

Pro Asp Cys Leu Arg Ala Cys Gln Glu Gln Ile Glu Ala Leu Leu Glu
        275                 280                 285

Ser Ser Leu Arg Gln Ala Gln Gln Asn Met Asp Pro Lys Ala Ala Glu
    290                 295                 300

Glu Glu Glu Glu Glu Glu Glu Glu Glu Glu Val Asp Leu Ala Cys Thr
305                 310                 315                 320

Pro Thr Asp Val Arg Asp Val Asp Ile Ala Ser Lys Gly Gly Gly Gly
                325                 330                 335

Ser Gly Gly Gly Gly Ser Gly Gly Gly Gly Ser Met Ala Thr Ser Arg
            340                 345                 350

Tyr Glu Pro Val Ala Glu Ile Gly Val Gly Ala Tyr Gly Thr Val Tyr
            355                 360                 365

Lys Ala Arg Asp Pro His Ser Gly His Phe Val Ala Leu Lys Ser Val
370                 375                 380

Arg Val Pro Asn Gly Gly Gly Gly Gly Gly Leu Pro Ile Ser Thr
385                 390                 395                 400

Val Arg Glu Val Ala Leu Leu Arg Arg Leu Glu Ala Phe Glu His Pro
                405                 410                 415

Asn Val Val Arg Leu Met Asp Val Cys Ala Thr Ser Arg Thr Asp Arg
            420                 425                 430

Glu Ile Lys Val Thr Leu Val Phe Glu His Val Asp Gln Asp Leu Arg
        435                 440                 445

Thr Tyr Leu Asp Lys Ala Pro Pro Pro Gly Leu Pro Ala Glu Thr Ile
450                 455                 460

Lys Asp Leu Met Arg Gln Phe Leu Arg Gly Leu Asp Phe Leu His Ala
```

```
              465                       470                       475                       480
     Asn  Cys  Ile  Val  His  Arg  Asp  Leu  Lys  Pro  Glu  Asn  Ile  Leu  Val  Thr
                         485                      490                      495

Ser  Gly  Gly  Thr  Val  Lys  Leu  Ala  Asp  Phe  Gly  Leu  Ala  Arg  Ile  Tyr
                    500                      505                      510

Ser  Tyr  Gln  Met  Ala  Leu  Thr  Pro  Val  Val  Val  Thr  Leu  Trp  Tyr  Arg
               515                      520                      525

Ala  Pro  Glu  Val  Leu  Leu  Gln  Ser  Thr  Tyr  Ala  Thr  Pro  Val  Asp  Met
          530                      535                      540

Trp  Ser  Val  Gly  Cys  Ile  Phe  Ala  Glu  Met  Phe  Arg  Arg  Lys  Pro  Leu
     545                      550                      555                      560

Phe  Cys  Gly  Asn  Ser  Glu  Ala  Asp  Gln  Leu  Gly  Lys  Ile  Phe  Asp  Leu
                         565                      570                      575

Ile  Gly  Leu  Pro  Pro  Glu  Asp  Asp  Trp  Pro  Arg  Asp  Val  Ser  Leu  Pro
                    580                      585                      590

Arg  Gly  Ala  Phe  Pro  Pro  Arg  Gly  Pro  Arg  Pro  Val  Gln  Ser  Val  Val
               595                      600                      605

Pro  Glu  Met  Glu  Glu  Ser  Gly  Ala  Gln  Leu  Leu  Leu  Glu  Met  Leu  Thr
          610                      615                      620

Phe  Asn  Pro  His  Lys  Arg  Ile  Ser  Ala  Phe  Arg  Ala  Leu  Gln  His  Ser
     625                      630                      635                      640

Tyr  Leu  His  Lys  Asp  Glu  Gly  Asn  Pro  Glu  Gly  Gly  Ser  Ala  Trp  Arg
                         645                      650                      655

His  Pro  Gln  Phe  Gly  Gly
                    660
```

( 2 ) INFORMATION FOR SEQ ID NO:6:

( i ) SEQUENCE CHARACTERISTICS:
        ( A ) LENGTH: 4540 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

```
GACGAAAGGG   CCTCGTGATA   CGCCTATTTT   TATAGGTTAA   TGTCATGATA   ATAATGGTTT       60
CTTAGACGTC   AGGTGGCACT   TTTCGGGGAA   ATGTGCGCGG   AACCCCTATT   TGTTTATTTT      120
TCTAAATACA   TTCAAATATG   TATCCGCTCA   TGAGACAATA   ACCCTGATAA   ATGCTTCAAT      180
AATATTGAAA   AAGGAAGAGT   ATGAGTATTC   AACATTTCCG   TGTCGCCCTT   ATTCCCTTTT      240
TTGCGGCATT   TTGCCTTCCT   GTTTTTGCTC   ACCCAGAAAC   GCTGGTGAAA   GTAAAAGATG      300
CTGAAGATCA   GTTGGGTGCA   CGAGTGGGTT   ACATCGAACT   GGATCTCAAC   AGCGGTAAGA      360
TCCTTGAGAG   TTTTCGCCCC   GAAGAACGTT   TTCCAATGAT   GAGCACTTTT   AAAGTTCTGC      420
TATGTGGCGC   GGTATTATCC   CGTATTGACG   CCGGGCAAGA   GCAACTCGGT   CGCCGCATAC      480
ACTATTCTCA   GAATGACTTG   GTTGAGTACT   CACCAGTCAC   AGAAAAGCAT   CTTACGGATG      540
GCATGACAGT   AAGAGAATTA   TGCAGTGCTG   CCATAACCAT   GAGTGATAAC   ACTGCGGCCA      600
ACTTACTTCT   GACAACGATC   GGAGGACCGA   AGGAGCTAAC   CGCTTTTTTG   CACAACATGG      660
GGGATCATGT   AACTCGCCTT   GATCGTTGGG   AACCGGAGCT   GAATGAAGCC   ATACCAAACG      720
ACGAGCGTGA   CACCACGATG   CCTGTAGCAA   TGGCAACAAC   GTTGCGCAAA   CTATTAACTG      780
GCGAACTACT   TACTCTAGCT   TCCCGGCAAC   AATTAATAGA   CTGGATGGAG   GCGGATAAAG      840
TTGCAGGACC   ACTTCTGCGC   TCGGCCCTTC   CGGCTGGCTG   GTTTATTGCT   GATAAATCTG      900
```

| | | | | | | |
|---|---|---|---|---|---|---|
| GAGCCGGTGA | GCGTGGGTCT | CGCGGTATCA | TTGCAGCACT | GGGGCCAGAT | GGTAAGCCCT | 960 |
| CCCGTATCGT | AGTTATCTAC | ACGACGGGGA | GTCAGGCAAC | TATGGATGAA | CGAAATAGAC | 1020 |
| AGATCGCTGA | GATAGGTGCC | TCACTGATTA | AGCATTGGTA | ACTGTCAGAC | CAAGTTTACT | 1080 |
| CATATATACT | TTAGATTGAT | TTAAAACTTC | ATTTTAATT | TAAAAGGATC | TAGGTGAAGA | 1140 |
| TCCTTTTTGA | TAATCTCATG | ACCAAAATCC | CTTAACGTGA | GTTTTCGTTC | CACTGAGCGT | 1200 |
| CAGACCCCGT | AGAAAAGATC | AAAGGATCTT | CTTGAGATCC | TTTTTTTCTG | CGCGTAATCT | 1260 |
| GCTGCTTGCA | AACAAAAAAA | CCACCGCTAC | CAGCGGTGGT | TTGTTTGCCG | GATCAAGAGC | 1320 |
| TACCAACTCT | TTTTCCGAAG | GTAACTGGCT | TCAGCAGAGC | GCAGATACCA | AATACTGTCC | 1380 |
| TTCTAGTGTA | GCCGTAGTTA | GGCCACCACT | TCAAGAACTC | TGTAGCACCG | CCTACATACC | 1440 |
| TCGCTCTGCT | AATCCTGTTA | CCAGTGGCTG | CTGCCAGTGG | CGATAAGTCG | TGTCTTACCG | 1500 |
| GGTTGGACTC | AAGACGATAG | TTACCGGATA | AGGCGCAGCG | GTCGGGCTGA | ACGGGGGGTT | 1560 |
| CGTGCACACA | GCCCAGCTTG | GAGCGAACGA | CCTACACCGA | ACTGAGATAC | CTACAGCGTG | 1620 |
| AGCATTGAGA | AAGCGCCACG | CTTCCCGAAG | GGAGAAAGGC | GGACAGGTAT | CCGGTAAGCG | 1680 |
| GCAGGGTCGG | AACAGGAGAG | CGCACGAGGG | AGCTTCCAGG | GGGAAACGCC | TGGTATCTTT | 1740 |
| ATAGTCCTGT | CGGGTTTCGC | CACCTCTGAC | TTGAGCGTCG | ATTTTTGTGA | TGCTCGTCAG | 1800 |
| GGGGGCGGAG | CCTATGGAAA | AACGCCAGCA | ACGCGGCCTT | TTTACGGTTC | CTGGCCTTTT | 1860 |
| GCTGGCCTTT | TGCTCACATG | TTCTTTCCTG | CGTTATCCCC | TGATTCTGTG | GATAACCGTA | 1920 |
| TTACCGCCTT | TGAGTGAGCT | GATACCGCTC | GCCGCAGCCG | AACGACCGAG | CGCAGCGAGT | 1980 |
| CAGTGAGCGA | GGAAGCGGAA | GAGCGCCCAA | TACGCAAACC | GCCTCTCCCC | GCGCGTTGGC | 2040 |
| CGATTCATTA | ATGCAGCTGG | CACGACAGGT | TTCCCGACTG | GAAAGCGGGC | AGTGAGCGCA | 2100 |
| ACGCAATTAA | TGTGAGTTAG | CTCACTCATT | AGGCACCCCA | GGCTTTACAC | TTTATGCTTC | 2160 |
| CGGCTCGTAT | GTTGTGTGGA | ATTGTGAGCG | GATAACAATT | TCACACAGGA | AACAGCTATG | 2220 |
| ACCATGATTA | CGCCAAGCTT | ACGGCGCGCC | GCCGCCACCA | TGGCGCATCA | TCATCATCAT | 2280 |
| CATGGAGGTG | GAGGTTCGGA | GCAGAAGCTT | ATTTCCGAGG | AGGATCTGCT | GGTGCCACGC | 2340 |
| GGTTCCCTGC | TAGCAATGGA | ACACCAGCTC | CTGTGCTGCG | AAGTGGAAAC | CATCCGCCGC | 2400 |
| GCGTACCCCG | ATGCCAACCT | CCTCAACGAC | CGGGTGCTGC | GGGCCATGCT | AAAGGCGGAG | 2460 |
| GAGACCTGCG | CGCCCTCGGT | GTCCTACTTC | AAATGTGTGC | AAAAGGAGGT | CCTGCCGTCC | 2520 |
| ATGCGGAAGA | TCGTCGCCAC | CTGGATGCTG | GAGGTCTGCG | AGGAACAGAA | GTGCGAGGAG | 2580 |
| GAGGTCTTCC | CGCTGGCCAT | GAACTACCTG | GACCGCTTCC | TGTCGCTGGA | GCCCGTGAAA | 2640 |
| AAGAGCCGCC | TGCAGCTGCT | GGGGGCCACT | TGCATGTTCG | TGGCCTCTAA | GATGAAGGAG | 2700 |
| ACCATCCCCC | TGACGGCCGA | GAAGCTGTGC | ATCTACACCG | ACAACTCCAT | CCGGCCCGAG | 2760 |
| GAGCTGCTGC | AAATGGAGCT | GCTCCTGGTG | AACAAGCTCA | AGTGGAACCT | GGCCGCAATG | 2820 |
| ACCCCGCACG | ATTTCATTGA | ACACTTCCTC | TCCAAAATGC | CAGAGGCGGA | GGAGAACAAA | 2880 |
| CAGATCATCC | GCAAACACGC | GCAGACCTTC | GTTGCCCTCT | GTGCCACAGA | TGTGAAGTTC | 2940 |
| ATTTCCAATC | CGCCCTCCAT | GGTGGCAGCG | GGGAGCGTGG | TGGCCGCAGT | GCAAGGCCTG | 3000 |
| AACCTGAGGA | GCCCCAACAA | CTTCCTGTCC | TACTACCGCC | TCACACGCTT | CCTCTCCAGA | 3060 |
| GTGATCAAGT | GTGACCCAGA | CTGCCTCCGG | GCCTGCCAGG | AGCAGATCGA | AGCCCTGCTG | 3120 |
| GAGTCAAGCC | TGCGCCAGGC | CCAGCAGAAC | ATGGACCCCA | AGGCCGCCGA | GGAGGAGGAG | 3180 |
| GAGGAAGAGG | AGGAAGAGGA | GGTGGACCTG | GCTTGCACAC | CCACCGACGT | GCGGGACGTG | 3240 |
| GACATCGCAT | CGATGGGTGG | AGGTTCTGGT | GGAGGTTCTG | GTGGAGGTTC | TGGTGGAGGT | 3300 |

| | | | | | |
|---|---|---|---|---|---|
| TCTGGTGGAG | GTTCTGGTGG | AGGTTCTGGC | TTAAGTTCGA | AGGGTGGTGG | AGGTTCTGGA | 3360 |
| GGTGGAGGAT | CCGGTGGTGG | AGGTTCGATG | GCTACCTCTC | GATATGAGCC | AGTGGCTGAA | 3420 |
| ATTGGTGTCG | GTGCCTATGG | GACAGTGTAC | AAGGCCCGTG | ATCCCCACAG | TGGCCACTTT | 3480 |
| GTGGCCCTCA | AGAGTGTGAG | AGTCCCCAAT | GGAGGAGGAG | GTGGAGGAGG | CCTTCCCATC | 3540 |
| AGCACAGTTC | GTGAGGTGGC | TTTACTGAGG | CGACTGGAGG | CTTTTGAGCA | TCCCAATGTT | 3600 |
| GTCCGGCTGA | TGGACGTCTG | TGCCACATCC | CGAACTGACC | GGGAGATCAA | GGTAACCCTG | 3660 |
| GTGTTTGAGC | ATGTAGACCA | GGACCTAAGG | ACATATCTGG | ACAAGGCACC | CCCACCAGGC | 3720 |
| TTGCCAGCCG | AAACGATCAA | GGATCTGATG | CGCCAGTTTC | TAAGAGGCCT | AGATTTCCTT | 3780 |
| CATGCCAATT | GCATCGTTCA | CCGAGATCTG | AAGCCAGAGA | ACATTCTGGT | GACAAGTGGT | 3840 |
| GGAACAGTCA | AGCTGGCTGA | CTTTGGCCTG | GCCAGAATCT | ACAGCTACCA | GATGGCACTT | 3900 |
| ACACCCGTGG | TTGTTACACT | CTGGTACCGA | GCTCCCGAAG | TTCTTCTGCA | GTCCACATAT | 3960 |
| GCAACACCTG | TGGACATGTG | GAGTGTTGGC | TGTATCTTTG | CAGAGATGTT | TCGTCGAAAG | 4020 |
| CCTCTCTTCT | GTGGAAACTC | TGAAGCCGAC | CAGTTGGGCA | AAATCTTTGA | CCTGATTGGG | 4080 |
| CTGCCTCCAG | AGGATGACTG | GCCTCGAGAT | GTATCCCTGC | CCCGTGGAGC | CTTTCCCCCC | 4140 |
| AGAGGGCCCC | GCCCAGTGCA | GTCGGTGGTA | CCTGAGATGG | AGGAGTCGGG | AGCACAGCTG | 4200 |
| CTGCTGGAAA | TGCTGACTTT | TAACCCACAC | AAGCGAATCT | CTGCCTTTCG | AGCTCTGCAG | 4260 |
| CACTCTTATC | TACATAAGGA | TGAAGGTAAT | CCGGAGGGCG | GCAGCGCTTG | GCGCCACCCA | 4320 |
| CAGTTCGGTG | GTTGAATAAA | TAGATGAATG | ACCTGCAGGT | GCACTCTCAG | TACAATCTGC | 4380 |
| TCTGATGCCG | CATAGTTAAG | CCAGCCCCGA | CACCCGCCAA | CACCCGCTGA | CGCGCCCTGA | 4440 |
| CGGGCTTGTC | TGCTCCCGGC | ATCCGCTTAC | AGACAAGCTG | TGACCGTCTC | CGGGAGCTGC | 4500 |
| ATGTGTCAGA | GGTTTTCACC | GTCATCACCG | AAACGCGCGA | | | 4540 |

( 2 ) INFORMATION FOR SEQ ID NO:7:

( i ) SEQUENCE CHARACTERISTICS:
        ( A ) LENGTH: 705 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Met Thr Met Ile Thr Pro Ser Leu Arg Arg Ala Ala Ala Thr Met Ala
 1               5                  10                  15

His His His His His His Gly Gly Gly Ser Glu Gln Lys Leu Ile
            20                  25                  30

Ser Glu Glu Asp Leu Leu Val Pro Arg Gly Ser Leu Leu Ala Met Glu
        35                  40                  45

His Gln Leu Leu Cys Cys Glu Val Glu Thr Ile Arg Arg Ala Tyr Pro
    50                  55                  60

Asp Ala Asn Leu Leu Asn Asp Arg Val Leu Arg Ala Met Leu Lys Ala
65                  70                  75                  80

Glu Glu Thr Cys Ala Pro Ser Val Ser Tyr Phe Lys Cys Val Gln Lys
                85                  90                  95

Glu Val Leu Pro Ser Met Arg Lys Ile Val Ala Thr Trp Met Leu Glu
            100                 105                 110

Val Cys Glu Glu Gln Lys Cys Glu Glu Glu Val Phe Pro Leu Ala Met
        115                 120                 125
```

-continued

```
Asn  Tyr  Leu  Asp  Arg  Phe  Leu  Ser  Leu  Glu  Pro  Val  Lys  Lys  Ser  Arg
     130                 135                 140

Leu  Gln  Leu  Leu  Gly  Ala  Thr  Cys  Met  Phe  Val  Ala  Ser  Lys  Met  Lys
145                      150                 155                      160

Glu  Thr  Ile  Pro  Leu  Thr  Ala  Glu  Lys  Leu  Cys  Ile  Tyr  Thr  Asp  Asn
                    165                 170                      175

Ser  Ile  Arg  Pro  Glu  Glu  Leu  Leu  Gln  Met  Glu  Leu  Leu  Leu  Val  Asn
                    180                 185                 190

Lys  Leu  Lys  Trp  Asn  Leu  Ala  Ala  Met  Thr  Pro  His  Asp  Phe  Ile  Glu
               195                 200                 205

His  Phe  Leu  Ser  Lys  Met  Pro  Glu  Ala  Glu  Glu  Asn  Lys  Gln  Ile  Ile
     210                 215                      220

Arg  Lys  His  Ala  Gln  Thr  Phe  Val  Ala  Leu  Cys  Ala  Thr  Asp  Val  Lys
225                      230                 235                      240

Phe  Ile  Ser  Asn  Pro  Pro  Ser  Met  Val  Ala  Ala  Gly  Ser  Val  Val  Ala
                    245                 250                      255

Ala  Val  Gln  Gly  Leu  Asn  Leu  Arg  Ser  Pro  Asn  Asn  Phe  Leu  Ser  Tyr
               260                 265                      270

Tyr  Arg  Leu  Thr  Arg  Phe  Leu  Ser  Arg  Val  Ile  Lys  Cys  Asp  Pro  Asp
          275                 280                 285

Cys  Leu  Arg  Ala  Cys  Gln  Glu  Gln  Ile  Glu  Ala  Leu  Leu  Glu  Ser  Ser
     290                 295                 300

Leu  Arg  Gln  Ala  Gln  Gln  Asn  Met  Asp  Pro  Lys  Ala  Ala  Glu  Glu  Glu
305                      310                 315                      320

Glu  Glu  Glu  Glu  Glu  Glu  Glu  Glu  Val  Asp  Leu  Ala  Cys  Thr  Pro  Thr
                    325                 330                      335

Asp  Val  Arg  Asp  Val  Asp  Ile  Ala  Ser  Met  Gly  Gly  Gly  Ser  Gly  Gly
               340                 345                      350

Gly  Ser  Gly  Gly  Gly  Ser  Gly  Gly  Gly  Ser  Gly  Gly  Gly  Ser  Gly  Gly
          355                 360                 365

Gly  Ser  Gly  Leu  Ser  Ser  Lys  Gly  Gly  Gly  Gly  Ser  Gly  Gly  Gly  Gly
          370                 375                      380

Ser  Gly  Gly  Gly  Gly  Ser  Met  Ala  Thr  Ser  Arg  Tyr  Glu  Pro  Val  Ala
385                      390                 395                      400

Glu  Ile  Gly  Val  Gly  Ala  Tyr  Gly  Thr  Val  Tyr  Lys  Ala  Arg  Asp  Pro
                    405                 410                      415

His  Ser  Gly  His  Phe  Val  Ala  Leu  Lys  Ser  Val  Arg  Val  Pro  Asn  Gly
               420                 425                 430

Gly  Gly  Gly  Gly  Gly  Gly  Leu  Pro  Ile  Ser  Thr  Val  Arg  Glu  Val  Ala
          435                 440                 445

Leu  Leu  Arg  Arg  Leu  Glu  Ala  Phe  Glu  His  Pro  Asn  Val  Val  Arg  Leu
     450                 455                 460

Met  Asp  Val  Cys  Ala  Thr  Ser  Arg  Thr  Asp  Arg  Glu  Ile  Lys  Val  Thr
465                      470                 475                      480

Leu  Val  Phe  Glu  His  Val  Asp  Gln  Asp  Leu  Arg  Thr  Tyr  Leu  Asp  Lys
                    485                 490                      495

Ala  Pro  Pro  Pro  Gly  Leu  Pro  Ala  Glu  Thr  Ile  Lys  Asp  Leu  Met  Arg
                    500                 505                      510

Gln  Phe  Leu  Arg  Gly  Leu  Asp  Phe  Leu  His  Ala  Asn  Cys  Ile  Val  His
          515                 520                      525

Arg  Asp  Leu  Lys  Pro  Glu  Asn  Ile  Leu  Val  Thr  Ser  Gly  Gly  Thr  Val
530                      535                      540

Lys  Leu  Ala  Asp  Phe  Gly  Leu  Ala  Arg  Ile  Tyr  Ser  Tyr  Gln  Met  Ala
545                 550                 555                      560
```

```
Leu  Thr  Pro  Val  Val  Thr  Leu  Trp  Tyr  Arg  Ala  Pro  Glu  Val  Leu
               565            570                           575

Leu  Gln  Ser  Thr  Tyr  Ala  Thr  Pro  Val  Asp  Met  Trp  Ser  Val  Gly  Cys
               580                 585                      590

Ile  Phe  Ala  Glu  Met  Phe  Arg  Arg  Lys  Pro  Leu  Phe  Cys  Gly  Asn  Ser
          595                      600                      605

Glu  Ala  Asp  Gln  Leu  Gly  Lys  Ile  Phe  Asp  Leu  Ile  Gly  Leu  Pro  Pro
          610                      615                 620

Glu  Asp  Asp  Trp  Pro  Arg  Asp  Val  Ser  Leu  Pro  Arg  Gly  Ala  Phe  Pro
625                      630                      635                      640

Pro  Arg  Gly  Pro  Arg  Pro  Val  Gln  Ser  Val  Val  Pro  Glu  Met  Glu  Glu
                    645                      650                      655

Ser  Gly  Ala  Gln  Leu  Leu  Leu  Glu  Met  Leu  Thr  Phe  Asn  Pro  His  Lys
               660                 665                      670

Arg  Ile  Ser  Ala  Phe  Arg  Ala  Leu  Gln  His  Ser  Tyr  Leu  His  Lys  Asp
          675                      680                      685

Glu  Gly  Asn  Pro  Glu  Gly  Gly  Ser  Ala  Trp  Arg  His  Pro  Gln  Phe  Gly
          690                 695                      700

Gly

705
```

(2) INFORMATION FOR SEQ ID NO:8:

(i) SEQUENCE CHARACTERISTICS:
        (A) LENGTH: 647 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Met  Glu  His  Gln  Leu  Leu  Cys  Cys  Glu  Val  Glu  Thr  Ile  Arg  Arg  Ala
1               5                       10                      15

Tyr  Pro  Asp  Ala  Asn  Leu  Leu  Asn  Asp  Arg  Val  Leu  Arg  Ala  Met  Leu
               20                 25                      30

Lys  Ala  Glu  Glu  Thr  Cys  Ala  Pro  Ser  Val  Ser  Tyr  Phe  Lys  Cys  Val
          35                      40                      45

Gln  Lys  Glu  Val  Leu  Pro  Ser  Met  Arg  Lys  Ile  Val  Ala  Thr  Trp  Met
     50                      55                      60

Leu  Glu  Val  Cys  Glu  Glu  Gln  Lys  Cys  Glu  Glu  Glu  Val  Phe  Pro  Leu
65                      70                      75                      80

Ala  Met  Asn  Tyr  Leu  Asp  Arg  Phe  Leu  Ser  Leu  Glu  Pro  Val  Lys  Lys
               85                      90                      95

Ser  Arg  Leu  Gln  Leu  Leu  Gly  Ala  Thr  Cys  Met  Phe  Val  Ala  Ser  Lys
               100                     105                     110

Met  Lys  Glu  Thr  Ile  Pro  Leu  Thr  Ala  Glu  Lys  Leu  Cys  Ile  Tyr  Thr
          115                     120                     125

Asp  Asn  Ser  Ile  Arg  Pro  Glu  Glu  Leu  Leu  Gln  Met  Glu  Leu  Leu  Leu
          130                     135                     140

Val  Asn  Lys  Leu  Lys  Trp  Asn  Leu  Ala  Ala  Met  Thr  Pro  His  Asp  Phe
145                     150                     155                     160

Ile  Glu  His  Phe  Leu  Ser  Lys  Met  Pro  Glu  Ala  Glu  Glu  Asn  Lys  Gln
               165                     170                     175

Ile  Ile  Arg  Lys  His  Ala  Gln  Thr  Phe  Val  Ala  Leu  Cys  Ala  Thr  Asp
               180                     185                     190
```

| | | | | | | | | | | | | | | |
|---|---|---|---|---|---|---|---|---|---|---|---|---|---|---|
| Val | Lys | Phe 195 | Ile | Ser | Asn | Pro | Pro 200 | Ser | Met | Val | Ala | Ala 205 | Gly | Ser | Val |
| Val | Ala 210 | Ala | Val | Gln | Gly 215 | Leu | Asn | Leu | Arg | Ser 220 | Pro | Asn | Asn | Phe | Leu |
| Ser 225 | Tyr | Tyr | Arg | Leu | Thr 230 | Arg | Phe | Leu | Ser | Arg 235 | Val | Ile | Lys | Cys | Asp 240 |
| Pro | Asp | Cys | Leu | Arg 245 | Ala | Cys | Gln | Glu | Ile 250 | Glu | Ala | Leu | Leu 255 | Glu | |
| Ser | Ser | Leu | Arg 260 | Gln | Ala | Gln | Gln | Asn 265 | Met | Asp | Pro | Lys 270 | Ala | Ala | Glu |
| Glu | Glu | Glu 275 | Glu | Glu | Glu | Glu | Glu 280 | Glu | Glu | Val | Asp | Leu 285 | Ala | Cys | Thr |
| Pro | Thr 290 | Asp | Val | Arg | Asp | Val 295 | Asp | Ile | Ala | Ser | Met 300 | Gly | Gly | Gly | Ser |
| Gly 305 | Gly | Gly | Ser | Gly | Gly 310 | Gly | Ser | Gly | Gly | Gly 315 | Ser | Gly | Gly | Gly | Ser 320 |
| Gly | Gly | Gly | Ser | Gly 325 | Leu | Ser | Ser | Lys | Gly 330 | Gly | Gly | Ser | Gly 335 | Gly | |
| Gly | Gly | Ser | Gly 340 | Gly | Gly | Gly | Ser | Met 345 | Ala | Thr | Ser | Arg | Tyr 350 | Glu | Pro |
| Val | Ala | Glu 355 | Ile | Gly | Val | Gly | Ala 360 | Tyr | Gly | Thr | Val | Tyr 365 | Lys | Ala | Arg |
| Asp | Pro 370 | His | Ser | Gly | His | Phe 375 | Val | Ala | Leu | Lys | Ser 380 | Val | Arg | Val | Pro |
| Asn 385 | Gly | Gly | Gly | Gly | Gly 390 | Gly | Gly | Leu | Pro | Ile 395 | Ser | Thr | Val | Arg | Glu 400 |
| Val | Ala | Leu | Leu | Arg 405 | Arg | Leu | Glu | Ala | Phe 410 | Glu | His | Pro | Asn | Val 415 | Val |
| Arg | Leu | Met | Asp 420 | Val | Cys | Ala | Thr | Ser 425 | Arg | Thr | Asp | Arg | Glu 430 | Ile | Lys |
| Val | Thr | Leu 435 | Val | Phe | Glu | His | Val 440 | Asp | Gln | Asp | Leu | Arg 445 | Thr | Tyr | Leu |
| Asp | Lys 450 | Ala | Pro | Pro | Pro | Gly 455 | Leu | Pro | Ala | Glu | Thr 460 | Ile | Lys | Asp | Leu |
| Met 465 | Arg | Gln | Phe | Leu | Arg 470 | Gly | Leu | Asp | Phe | Leu 475 | His | Ala | Asn | Cys | Ile 480 |
| Val | His | Arg | Asp | Leu 485 | Lys | Pro | Glu | Asn | Ile 490 | Leu | Val | Thr | Ser | Gly 495 | Gly |
| Thr | Val | Lys | Leu 500 | Ala | Asp | Phe | Gly | Leu 505 | Ala | Arg | Ile | Tyr | Ser 510 | Tyr | Gln |
| Met | Ala | Leu 515 | Thr | Pro | Val | Val | Val 520 | Thr | Leu | Trp | Tyr | Arg 525 | Ala | Pro | Glu |
| Val | Leu 530 | Leu | Gln | Ser | Thr | Tyr 535 | Ala | Thr | Pro | Val | Asp 540 | Met | Trp | Ser | Val |
| Gly 545 | Cys | Ile | Phe | Ala | Glu 550 | Met | Phe | Arg | Arg | Lys 555 | Pro | Leu | Phe | Cys | Gly 560 |
| Asn | Ser | Glu | Ala | Asp 565 | Gln | Leu | Gly | Lys | Ile 570 | Phe | Asp | Leu | Ile 575 | Gly | Leu |
| Pro | Pro | Glu | Asp 580 | Asp | Trp | Pro | Arg | Asp 585 | Val | Ser | Leu | Pro | Arg 590 | Gly | Ala |
| Phe | Pro | Pro | Arg 595 | Gly | Pro | Arg | Pro | Val 600 | Gln | Ser | Val | Val 605 | Pro | Glu | Met |
| Glu | Glu | Ser | Gly | Ala | Gln | Leu | Leu | Leu | Glu | Met | Leu | Thr | Phe | Asn | Pro |

|  |  |  |  |  |  |  |  |  |  |  |  |  |  |  |
|---|---|---|---|---|---|---|---|---|---|---|---|---|---|---|
|  |  | 610 |  |  | 615 |  |  |  |  | 620 |  |  |  |  |
| His 625 | Lys | Arg | Ile | Ser | Ala 630 | Phe | Arg | Ala | Leu | Gln 635 | His | Ser | Tyr | Leu | His 640 |
| Lys | Asp | Glu | Gly | Asn 645 | Pro | Glu | | | | | | | | |